US010472684B2

(12) United States Patent
Barten et al.

(10) Patent No.: US 10,472,684 B2
(45) Date of Patent: Nov. 12, 2019

(54) METHODS AND COMPOSITIONS FOR PRODUCING BRACHYTIC CORN PLANTS

(71) Applicant: Monsanto Technology LLC, St. Louis, MO (US)

(72) Inventors: Ty Jason Barten, St. Louis, MO (US); Alana N. Brown, St. Louis, MO (US); Edward James Cargill, St. Louis, MO (US); Romain Fouquet, Saint-Palais (FR); Jose Rafael Gomez, Zapopan (MX); Matthew Sean Marengo, St. Louis, MO (US); Manuel Oyervides Garcia, El Palomar (MX); Jeanette M. Peevers, St. Louis, MO (US); Dennis Hung Yang, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 518 days.

(21) Appl. No.: 15/139,733

(22) Filed: Apr. 27, 2016

(65) Prior Publication Data
US 2016/0319375 A1 Nov. 3, 2016

Related U.S. Application Data

(60) Provisional application No. 62/153,831, filed on Apr. 28, 2015, provisional application No. 62/180,430, filed on Jun. 16, 2015.

(51) Int. Cl.
C12Q 1/6895 (2018.01)
A01H 1/04 (2006.01)
A01H 5/10 (2018.01)

(52) U.S. Cl.
CPC .............. C12Q 1/6895 (2013.01); A01H 1/04 (2013.01); A01H 5/10 (2013.01); C12Q 2600/13 (2013.01); C12Q 2600/156 (2013.01); C12Q 2600/172 (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. | |
| 5,217,863 A | 6/1993 | Cotton et al. | |
| 5,468,613 A | 11/1995 | Erlich et al. | |
| 5,563,055 A | 10/1996 | Townsend et al. | |
| 5,595,890 A | 1/1997 | Newton et al. | |
| 5,616,464 A | 4/1997 | Albagi et al. | |
| 5,762,876 A | 6/1998 | Lincoln et al. | |
| 5,800,944 A | 9/1998 | Blonsky et al. | |
| 5,876,930 A | 3/1999 | Livak et al. | |
| 5,945,283 A | 8/1999 | Kwok et al. | |
| 6,004,744 A | 12/1999 | Goelet et al. | |
| 6,013,431 A | 1/2000 | Söderlund et al. | |
| 6,030,787 A | 2/2000 | Livak et al. | |
| 6,090,558 A | 7/2000 | Butler et al. | |
| 6,503,710 B2 | 1/2003 | Gut et al. | |
| 6,613,509 B1 | 9/2003 | Chen | |
| 6,799,122 B2 | 9/2004 | Benson | |
| 6,913,879 B1 | 7/2005 | Schena | |
| 6,996,476 B2 | 2/2006 | Najarian | |
| 7,041,874 B2 * | 5/2006 | Johal | C07K 14/415 800/290 |
| 7,166,779 B1 | 1/2007 | Hall et al. | |
| 7,211,717 B1 | 5/2007 | Johnson et al. | |
| 7,238,476 B2 | 7/2007 | McKeown et al. | |
| 7,250,252 B2 | 7/2007 | Katz et al. | |
| 7,270,981 B2 | 9/2007 | Armes et al. | |
| 7,282,355 B2 | 10/2007 | Shi | |
| 7,297,485 B2 | 11/2007 | Bornarth et al. | |
| 7,312,039 B2 | 12/2007 | Barany et al. | |
| 2002/0162142 A1 | 10/2002 | Johal et al. | |
| 2006/0042527 A1 | 3/2006 | Deppermann | |
| 2006/0046244 A1 | 3/2006 | Deppermann | |
| 2006/0046264 A1 | 3/2006 | Deppermann et al. | |
| 2006/0048247 A1 | 3/2006 | Deppermann et al. | |
| 2006/0048248 A1 | 3/2006 | Deppermann | |
| 2007/0079397 A1 | 4/2007 | Johal et al. | |
| 2007/0204366 A1 | 8/2007 | Deppermann et al. | |
| 2011/0277137 A1 | 11/2011 | Boerboom et al. | |
| 2012/0264627 A1 | 10/2012 | Reinherz et al. | |
| 2012/0284857 A1 | 11/2012 | Olsen et al. | |

FOREIGN PATENT DOCUMENTS

CN 102373278 A 3/2012
WO WO 2014/152759 A2 9/2014

OTHER PUBLICATIONS

Poehlman et al. Breeding field crops. vol. 378. Ames: Iowa State University Press, 1995 (Chapter 18 Breeding Corn (Maize) p. 469-474. (Year: 1995).*
Agarwal et al. (Plant cell reports 27.4 (2008): 617-631). (Year: 2008).*
Xing et al. (Journal of experimental botany 66.13 (2015): 3791-3802). (Year: 2015).*
Souza et al. (Rev. Brasil. Genet. VIII, 3,523-533 (1985). (Year: 1985).*
Arús et al., "Marker-assisted selection," *Plant Breeding: Principles and Prospects*, 314-331 (1993).
Borevitz et al., "Large-Scale Identification of Single-Feature Polymorphisms in Complex Genomes," *Genome Research*, 13:513-523 (2003).

(Continued)

Primary Examiner — Charles Logsdon
(74) Attorney, Agent, or Firm — Matthew L. Madsen; Arnold & Porter Kaye Scholer LLP

(57) ABSTRACT

The present disclosure is in the field of plant breeding. The disclosure provides methods for breeding corn plants having a brachytic trait using marker-assisted selection. The disclosure further provides brachytic germplasm, markers associated with a brachytic trait for introgressing the trait into elite germplasm in a breeding program. This disclosure also provides brachytic or dwarf elite corn varieties having yield equal to or higher than conventional non-brachytic corn varieties.

15 Claims, No Drawings
Specification includes a Sequence Listing.

(56) References Cited

OTHER PUBLICATIONS

Camacho et al., "Defining and Identifying crop landraces," *Plant Genetic Resources: Characterization and Utilization*, 3(3):373-84 (2006).
Cassani et al., "The brachytic 2 and 3 maize double mutant shows alterations in plant growth and embryo development," *Plant Growth Regulation*, 64(2):185-92 (2011).
Cui et al., "Detecting single-feature polymorphisms using oligonucleotide arrays and robusti," *Bioinformatics Oxford Journals*, 21:3852-3858 (2005).
Dhaliwhal et al., "Comparative analysis of ABCB1 reveals novel structural and functional conservation between monocots and dicots," *Frontiers in Plant Science*, 5:1-10 (2014).
Flint-Garcia et al., "Structure of Linkage Disequilibrium in Plants," *Annual Review of Plant Biology*, 54:357-374 (2003).
Forestan et al., "The maize *PIN* gene family of auxin transporters," *Frontiers in Plant Science*, 3:1-23 (2012).
Gaj et al., "ZFN, TALEN, and CRISPR/Cas-based methods for genome engineering," *Cell Press*, 31(7):397-405 (2013).
GenBank Accession No. AY366085.
Gruber et al., "Vectors for Plant Transformation," *Methods in Plant Molecular Biology and Biotechnology*, 89-119 (1993).
Hedrick, "Gametic Disequilibrium Measures: Proceed With Caution," *Genetics*, 117:31-41 (1987).
Horsch et al., "A Simple and General Method for Transferring Genes into Plants," *Science*, 227:1229-1231 (1985).
International Search Report and Written Opinion dated Sep. 23, 2016 for International Patent Application No. PCT/US16/29492.
Jannink et al., "Association mapping in plant populations," *Quantitative Genetics, Genomics and Plant Breeding*, 59-68 (2002).
Jansen et al., "High Resolution of Quantitative Traits Into Multiple Loci via Interval Mapping," *Genetics*, 136:1447-1455 (1994).
Jansen et al., "Biometrics in Plant Breeding: Applications of Molecular Markers," *Proceedings of the Ninth Meeting of the Eucarpia Section Biometrics in Plant Breeding*, 19-31 (1994).
Jansen et al., "Genotype-by-environment interaction in genetic mapping of multiple quantitative trait loci," *Theoretical and Applied Genetics*, 91:33-37 (1995).
Kempton, "Heritable Characters of Maize: III. Brachytic Culms," *Journal of Heredity*, 11:111-115 (1920).
Knoller et al., "Brachytic2/ZmABCB1 functions in IAA export from intercalary meristems," *Journal of Experimental Botany*, 61(13):3689-3696 (2010).
Kosambi, "The Estimation of Map Distances From Recombination Values," *Annals of Eugenics*, 12:172-75 (1944).
Kruglyak et al., "A Nonparametric Approach for Mapping Quantitative Trait Loci," *Genetics*, 139(3):1421-1428 (1995).
Lander et al., "Mapping Mendelian Factors Underlying Quantitative Traits Using RFLP Linkage Maps," *Genetics*, 121:185-199 (1989).
Mild et al., "Procedures for Introducing Foreign DNA into Plants," *Methods in Plant Molecular Biology and Biotechnology*, 67-88 (1993).
Multani et al., "Loss of an MDR Transporter in Compact Stalks of Maize br2 and Sorghum dw3 Mutants," *Science*, 302:81-84 (2003).
Openshaw et al., "Marker-assisted Selection in Backcross Breeding," *American Society for Horticultural Science/Crop Science of America*, 41-43 (1994).
Pilu et al., "Isolation and characterization of a new mutant allele of *brachvtic* 2 maize gene," *Molecular Breeding*, 20:83-91 (2007).
Ragot et al., "Marker-assisted backcrossing: a practical example," *Techniques et utilisations des marquers moleculaires*, 72:45-56 (1995).
Reddy, "Alternative Splicing of Pre-Messenger RNAs in Plants in the Genomic Era," *Annual Review of Plant Biology*, 58:267-294 (2007).
Reich et al., "Linkage disequilibrium in the human genome," *Nature*, 411:199-204 (2001).
Schaeffer, "Breeding Potential of Semi-dwarf Corn for Grain and Forage in the Northern U.S. Corn Belt," *University of Minnesota*, 1:16 (2012).
Service, "Gene sequencing: The Race for the $1000 Genome," *Science*, 311:1544-46 (2006).
(1994) Herewith.Utz et al., "Comparison of different approaches to interval mapping of quantitative trait loci," *Proceedings of the Ninth Meeting of the Eucarpia Section Biometrics in Plant Breeding*, 195-204 (1994).
Villa et al., "Defining and identifying crop landraces,"*Plant Genetic Resources*, 3(3):373-384 (2006).
Xing et al., "A rare SNP mutation in *Brachytic2* moderately reduces plant height and increases yield potential maize," *Journal of Experimental Botany*, 1-2 (2015).
Zeng, "Precision Mapping of Quantitative Trait Loci," *Genetics*, 136:1457-1468 (1994).
Major, et al., "An Evaluation of the Corn Heat Unit System for the Short-Season Growing Regions Across Canada," *Can. J. Plant Sci.*, 63:121-130 (1983).
Balzan, S., "Characterization of a novel brachytic2 (br2) allele in maize." Abstract of Ph.D. thesis., published Feb. 1, 2016, available at paduaresearch.cab.unipd.it/9421/, downloaded Mar. 10, 2017, full thesis not publicly available until Jan. 29, 2019.
Balzan et al., "Genetic and phenotypic characterization of a novel brachytic2 allele of maize," *Plant Growth Regulation*, 86(1):81-92 (2018), published online Jun. 19, 2018.

* cited by examiner

US 10,472,684 B2

METHODS AND COMPOSITIONS FOR PRODUCING BRACHYTIC CORN PLANTS

CROSS-REFERENCE TO RELATED APPLICATIONS

This application claims priority benefit to U.S. Provisional Patent Application Nos. 62/153,831 and 62/180,430, filed on Apr. 28, 2015, and Jun. 16, 2015, respectively, which are incorporated herein by reference in their entirety.

INCORPORATION OF SEQUENCE LISTING

A sequence listing contained in the file named "P34302US02_2016-05-27.txt" which is 47,507 bytes (measured in MS-Windows®) and created on May 27, 2016, comprises 120 nucleotide sequences, is filed electronically herewith and incorporated by reference in its entirety.

BACKGROUND

A sustained increase in crop yield, e.g., in wheat and rice has been achieved in the past few decades. This increase is partly attributed to the use of fertilizers and pesticides as well as the introduction of semi-dominant dwarfing mutations which reduce plant height. Taller plants are more likely to lodge in response to heavy rainfall or wind, and the heavier inflorescences of high-yield elite breeds also make them more susceptible to lodging. In contrast, crops with a shorter stature are more resistant to lodging. Moreover, dwarf and semi-dwarf traits can also allow higher planting densities and help improve crop harvest index and nitrogen response. The introduction of dwarf varieties of wheat and rice served as a cornerstone of the so-called "Green revolution" of the late 20th century.

Maize (*Zea mays* L.), a member of the *Gramineae* genus, provides cylindrical stalks similar to those from other grasses. The maize stalks are thick and spongy inside and divided into parts called internodes and nodes. The number of nodes ranges from between 8 to 40 depending on the variety and growing conditions. Commercial hybrid maize normally grows to a height of typically more than 2 meters with each plant having either one or two ears. The ear normally grows about one-third of the way up the plant or about three feet from the ground. Consequently a maize plant, while providing a large ear in addition to a substantial leaf and stalk structure, can have a considerable mechanical stability problem. Reducing the height of a maize plant can improve the mechanical stability of the plant.

More than 40 monogenic dwarfing mutants have been described in maize. A majority of these mutants lead to great reductions in grain yield and, consequently, they have not been used to enhance crop yield in germplasm that is sensible to lodging. Therefore, an important goal in corn breeding is to identify and use dwarf or semi-dwarf mutations which confer a short stature without severely impacting other organs, especially reproductive organs (e.g., ears).

In maize, brachytic mutants show a short stature due to a shortening of the internode length without a corresponding reduction in the number of internodes or the number and size of other organs, including the leaves, ear and tassel. See Kempton *J. Hered.* 11:111-115(1920); Pilu et al., *Molecular Breeding,* 20:83-91(2007). Three brachytic mutants have been isolated in maize to date: brachytic1 (br1), brachytic2 (br2) and brachytic3 (br3). Both br1 and br3 mutations cause a reduction in corn plant height which has been thought too severe for commercial exploitation due to potential impacts over yield. In contrast, the br2 mutant has particular agronomic potential because of the shortening of the internodes of the lower stalk with no obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with Gibberellins, auxins, brassinosteroids and cytokinins, suggesting that the biosynthesis of these hormones is not modified by the br2 mutation.

Multani et al. identified the genomic sequence of the Br2 gene and deposited it under GenBank Accession No. AY366085. See *Science,* 302(5642)81-84 (2003). Br2 was annotated to encode a putative protein similar to adenosine triphosphate (ATP)-binding cassette transporters of the multidrug resistant (MDR) class of P-glycoproteins (PGPs). Pilu et al. reported a br2-23 allele having an 8-bp deletion in the 3' end of the Br2 gene and claimed a direct relationship between this deletion and the brachytic phenotype in their br2-23 plants. See Pilu et al., *Molecular Breeding,* 20:83-91(2007). Nevertheless, the use of brachytic mutations in corn has not been exploited commercially partly because of the severity of the available brachytic mutant alleles.

There is a need in corn breeding to identify corn germplasm that provides novel and commercially relevant brachytic mutant alleles, e.g., those conferring an intermediate brachytic phenotype and maintaining or improving kernel yield. There is also a need to develop polymorphic markers for monitoring and introgressing novel brachytic mutant alleles, and further develop agronomically elite corn lines comprising a brachytic trait for enhancing plant productivity.

SUMMARY

The present disclosure provides methods of selecting a corn plant or seed, which methods comprise (a) detecting in a population of corn plants or seeds a corn plant or seed comprising a brachytic allele at a polymorphic locus, wherein the polymorphic locus is associated with or linked to a marker selected from the group consisting of SEQ ID Nos: 1-22 and 86-109; and (b) selecting the corn plant or seed comprising the brachytic allele. In some aspects, these methods comprise detecting a brachytic allele at a polymorphic locus within about 20 cM, 10 cM, 5 cM, 1 cM, 0.5 cM, or less than 0.5 cM of the marker selected from the group consisting of SEQ ID Nos: 1-22 and 86-109. In some aspects, these methods comprise detecting a brachytic allele at a polymorphic locus within about 20 cM, 10 cM, 5 cM, 1 cM, 0.5 cM, or less than 0.5 cM of the marker selected from the group consisting of SEQ ID Nos: 5-8, 11-22, and 86-95. In other aspects, these methods comprise detecting a brachytic allele of a marker selected from the group consisting of SEQ ID Nos: 1-22 and 86-109. In some aspects, these methods comprise detecting a brachytic allele of a marker selected from the group consisting of SEQ ID Nos: 5-8, 9-22, and 86-95. In some aspects, these methods comprise detecting a brachytic allele of a marker selected from the group consisting of SEQ ID Nos: 7 and 95. In some aspects, the detected brachytic allele is selected from the group consisting of SEQ ID Nos: 27-48. In some aspects, these methods comprise crossing a first corn plant comprising the brachytic allele with a second corn plant to produce the population of corn plants or seeds. In other aspects, these methods further comprise backcrossing with the second corn plant. In some aspects, these methods select a corn plant or seed from a segregating population or a haploid breeding population. In other aspects, these methods select a corn plant or seed from one or more landraces or doubled-haploid populations. In some aspects, step (b) of these methods comprise using a marker assay provided herein. In other aspects, these methods further comprise genotyping the population of corn plants or seeds at one or more polymorphic sequences selected from the group consisting of SEQ ID Nos: 71-75. In further aspects, these methods further comprise detecting a brachytic allele of a marker selected from the group consisting of SEQ ID Nos: 71-75. In some aspects, the detected brachytic allele is selected from the group consisting of SEQ ID Nos: 76-80.

In one aspect, this disclosure provides methods of creating a population of corn plants comprising at least one allele associated with a brachytic trait, which methods comprise the steps of (a) genotyping a first population of corn plants, the population containing at least one allele associated with a brachytic trait, wherein the at least one brachytic allele is associated with a marker selected from the group consisting of SEQ ID Nos: 1-22 and 86-109; (b) selecting from the first population one or more corn plants containing at least one brachytic allele; and (c) producing from the selected corn plants a second population, thereby creating a population of corn plants comprising at least one brachytic allele. In some aspects, these methods comprise genotyping a locus for at least one brachytic allele within about 20 cM, 10 cM, 5 cM, 1 cM, 0.5 cM, or less than 0.5 cM of the marker selected from the group consisting of SEQ ID Nos: 1-22 and 86-109. In some aspects, these methods comprise genotyping a locus for at least one brachytic allele within about 20 cM, 10 cM, 5 cM, 1 cM, 0.5 cM, or less than 0.5 cM of the marker selected from the group consisting of SEQ ID Nos: 5-8, 11-22, and 86-95. In other aspects, these methods comprise genotyping a marker selected from the group consisting of SEQ ID Nos: 1-22 and 86-109. In some aspects, these methods comprise genotyping a locus for at least one brachytic allele of a marker selected from the group consisting of SEQ ID Nos: 5-8, 11-22, and 86-95. In some aspects, these methods comprise genotyping a locus for at least one brachytic allele of a marker selected from the group consisting of SEQ ID Nos: 7 and 95. In some aspects, the brachytic allele is selected from the group consisting of SEQ ID Nos: 27-48. In other aspects, these methods further comprise genotyping the first population of corn plants at one or more polymorphic sequences selected from the group consisting of SEQ ID Nos: 71-75. In some aspects, step (a) of these methods further comprise genotyping the first population of corn plants at one or more polymorphic sequences selected from the group consisting of SEQ ID Nos: 71-75. In further aspects, step (a) of these methods further comprise genotyping the first population of corn plants for a brachytic allele selected from the group consisting of SEQ ID Nos: 76-80.

In one aspect, this disclosure provides methods of selecting a corn plant or seed, which methods comprise: (a) genotyping a population of corn plants or seeds at a polymorphic locus associated with a marker selected from the group consisting of SEQ ID Nos: 1-22 and 86-109; and (b) selecting a corn plant or seed comprising a brachytic allele at said polymorphic locus. In some aspects, these methods comprise genotyping at a polymorphic locus within about 20 cM, 10 cM, 5 cM, 1 cM, 0.5 cM, or less than 0.5 cM of the marker selected from the group consisting of SEQ ID Nos: 1-22 and 86-109. In other aspects, these methods comprise genotyping a marker selected from the group consisting of SEQ ID Nos: 1-22 and 86-109. In some aspects, these methods comprise genotyping a locus within about 20 cM, 10 cM, 5 cM, 1 cM, 0.5 cM, or less than 0.5 cM of the marker selected from the group consisting of SEQ ID Nos: 5-8, 11-22, and 86-95. In some aspects, these methods comprise genotyping a locus selected from the group consisting of SEQ ID Nos: 5-8, 11-22, and 86-95. In some aspects, these methods comprise genotyping a locus selected from the group consisting of SEQ ID Nos: 7 and 95. In some aspects, a plant or seed selected by these methods comprises a brachytic allele selected from the group consisting of SEQ ID Nos: 27-48. In other aspects, these methods further comprise genotyping the population of corn plants or seeds at one or more polymorphic sequences selected from the group consisting of SEQ ID Nos: 71-75. In some aspects, step (a) of these methods further comprise genotyping the first population of corn plants at one or more polymorphic sequences selected from the group consisting of SEQ ID Nos: 71-75. In further aspects, step (a) of these methods further comprise genotyping the first population of corn plants for a brachytic allele selected from the group consisting of SEQ ID Nos: 76-80.

In one aspect, this disclosure provides methods of selecting a corn plant or seed, the method comprising: (a) isolating a nucleic acid from a corn plant or seed; (b) analyzing the nucleic acid to detect a polymorphic marker associated with a brachytic haplotype, the brachytic haplotype comprising one or more, two or more, three or more, four or more, five or more, six or more, seven or more, or eight or more brachytic alleles of markers selected from the group consisting of SEQ ID Nos: 1-22 and 86-109; and (c) selecting a corn plant or seed comprising the brachytic haplotype. In some aspects, these methods comprise detecting a polymorphic marker within about 20 cM, 10 cM, 5 cM, 1 cM, 0.5 cM, or less than 0.5 cM of the brachytic haplotype. In other aspects, these methods comprise detecting a brachytic haplotype comprising one or more, two or more, three or more, four or more, five or more, six or more, seven or more, or eight or more brachytic alleles of markers selected from the group consisting of SEQ ID Nos: 1-22 and 86-109. In some aspects, these methods comprise genotyping both loci SEQ ID Nos: 7 and 95. In some aspects, the brachytic haplotype comprises one or more, two or more, three or more, four or more, five or more, six or more, seven or more, or eight or more sequences selected from the group consisting of SEQ ID Nos: 27-48. In other aspects, these methods further comprise analyzing the nucleic acid to detect one or more polymorphic sequences selected from the group consisting of SEQ ID Nos: 71-75. In some aspects, step (b) of these methods further comprise analyzing the nucleic acid to detect one or more polymorphic sequences selected from the group consisting of SEQ ID Nos: 71-75. In further aspects, these methods further comprise analyzing the nucleic acid to detect one or more brachytic alleles selected from the group consisting of SEQ ID Nos: 76-80.

In one aspect, this disclosure provides methods of introgressing a brachytic trait into a corn variety, the method comprising: (a) crossing a first corn variety comprising a brachytic trait with a second corn variety not comprising the brachytic trait to produce one or more progeny corn plants; (b) analyzing the one or more progeny corn plants to detect a brachytic allele, wherein the brachytic allele is linked to a marker selected from the group consisting of SEQ ID Nos: 1-22 and 86-109; and (c) selecting a progeny corn plant comprising the brachytic allele. In some aspects, these methods comprise detecting a brachytic allele within about 20 cM, 10 cM, 5 cM, 1 cM, 0.5 cM, or less than 0.5 cM of the marker selected from the group consisting of SEQ ID Nos: 1-22 and 86-109. In some aspects, these methods comprise detecting a brachytic allele within about 20 cM, 10 cM, 5 cM, 1 cM, 0.5 cM, or less than 0.5 cM of the marker selected from the group consisting of SEQ ID Nos: 5-8, 11-22, and 86-95. In some aspects, these methods comprise detecting a brachytic allele of a locus selected from the group consisting of SEQ ID Nos: 5-8, 11-22, and 86-95. In some aspects, these methods comprise detecting a brachytic allele of a locus selected from the group consisting of SEQ ID Nos: 7 and 95. In other aspects, these methods comprise detecting a brachytic allele of a marker selected from the group consisting of SEQ ID Nos: 1-22, 71-75, and 86-109. In some aspects, the brachytic allele is selected from the group consisting of SEQ ID Nos: 27-48 and 76-80.

Corn plants or seeds selected or produced using methods disclosed herein can have a single gene conversion of the Br2 genomic region. In some aspects, the corn plants or seeds comprise a reduced level of Br2 mRNA or protein compared to a control plant not having the brachytic allele. In other aspects, the corn plants or seeds comprise reduced Br2 protein activity compared to a control plant not having the brachytic allele. In some aspects, the height of the selected plant at maturity is reduced for about 10%, 20%, 30%, 40%, 50%, 60%, or 70% compared to a control plant not having a brachytic allele. In other aspects, the yield of the selected plant is equal to or more than the yield of a control plant not having a brachytic allele. In some aspects, corn plants or seeds selected using these methods require about 5%, 10%, 15%, 20%, or 25% fewer heat units than control plants to reach anthesis. In other aspects, corn plants or seeds selected using these methods have a relative maturity of about 10%, 15%, 20%, 25%, 30%, 35%, 40%, or 45% fewer days than the relative maturity of control plants.

In another aspect, this disclosure provides hybrid brachytic, dwarf, or semi-dwarf corn plants, or plant parts thereof, comprising a brachytic allele characterizable by one or more sequences selected from the group consisting of SEQ ID Nos: 27-48. In some aspects, corn plants provided herein are elite lines. These elite lines can be transgenic or non-transgenic, inbreds or hybrids.

In one aspect, this disclosure provides a container of elite corn seeds comprising a brachytic allele characterizable by one or more sequences selected from the group consisting of SEQ ID Nos: 27-48. These seeds can be transgenic or non-transgenic. They can also be inbred or hybrid seeds.

BRIEF DESCRIPTION OF THE SEQUENCES

SEQ ID NOs: 1 to 22 list polymorphic marker sequences concordant with the brachytic trait. SEQ ID NOs: 23 to 26 list example primer and probe sequences for genotyping marker SEQ ID NO: 7. SEQ ID NOs: 27 to 48 list the corresponding example brachytic alleles as shown in Table 2. SEQ ID NOs: 49 to 70 list the corresponding example non-brachytic alleles as shown in Table 2. SEQ ID NOs: 71 to 75 list additional polymorphic marker sequences. SEQ ID NOs: 76 to 80 list the corresponding example brachytic alleles as shown in Table 7. SEQ ID NOs: 81 to 85 list the corresponding example non-brachytic alleles as shown in Table 7. SEQ ID NOs: 86 to 109 list additional Br2-associated polymorphic sequences. SEQ ID NOs: 112 to 116 list example primer and probe sequences for genotyping marker SEQ ID NO: 95. One of ordinary skill in the art would understand that polymorphic markers disclosed herein comprise various alleles which include, but are not limited to, the listed example alleles.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a "corn plant" or "maize plant" refers to a plant of species *Zea mays* L and includes all plant varieties that can be bred with corn, including wild maize species.

As used herein, a "dwarf" plant refers to a atypically small plant. Generally, such a "dwarf plant" has a stature or height that is reduced from that of a control wild-type plant (e.g., a sibling plant comprising all other traits except the dwarf trait) by about 30%, 35%, 40%, 45%, 50%, 55%, 60% or greater. A "semi-dwarf plant" refers to a plant having a stature or height that is reduced from that of a control wild-type plant by about 5%, 10%, 15%, 20%, 25%, 30% or less. Generally, but not exclusively, such a dwarf plant is characterized by a reduced stem, stalk or trunk length when compared to the control wild-type plant.

As used herein, a "brachytic plant" refers to a plant showing a short stature due to a shortening of the internode length without a corresponding reduction in the number of internodes or the number and size of other organs including, but not limited to, leaves, ear and tassel. "Brachysm" refers to a abnormal variation of plants characterized by shortening of the internodes, without corresponding reductions of other plant parts.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

As used herein, the phrase "associated with" or "linked to" refers to a recognizable and/or assayable relationship between two entities. For example, the phrase "associated with a brachytic trait" refers to a trait, locus, gene, allele, marker, phenotype, etc., or the expression thereof, the presence or absence of which can influence an extent, degree, and/or rate at which a plant or a part of interest thereof that has a brachytic trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a brachytic phenotype" refers to a marker whose presence or absence can be used to predict whether and to what extent a plant will display a brachytic phenotype.

As used herein, a centimorgan ("cM") is a unit of measure of recombination frequency and genetic distance between two loci. One cM is equal to a 1% chance that a marker at one genetic locus will be separated from a marker at, a second locus due to crossing over in a single generation. Genetic distances can be calculated from recombination values using the Kosambi function (Kosambi, The estimation of map distances from recombination values. *Annals of Eugenics*, 12:172-75 (1944)).

As used herein, "closely linked" means that the marker or locus is within about 20 cM, 10 cM, 5 cM, 1 cM, 0.5 cM, or less than 0.5 cM of another marker or locus. For example, 20 cM means that recombination between the marker and the locus with a frequency of equal to or less than about 20%.

As used herein, "locus" is a chromosome region where a polymorphic nucleic acid, trait determinant, gene or marker is located. A locus may represent a single nucleotide, a few nucleotides or a large number of nucleotides in a genomic region. The loci of this disclosure comprise one or more polymorphisms in a population; e.g., alternative alleles are present in some individuals. A "gene locus" is a specific chromosome location in the genome of a species where a specific gene can be found.

As used herein, "allele" refers to an alternative nucleic acid sequence at a particular locus. The length of an allele can be as small as 1 nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, a "brachytic allele" is an allele at a particular locus that confers, or contributes to, a brachytic phenotype, or alternatively, is an allele that allows for the identification of plants that comprise a brachytic phenotype or plants that can give rise to progenies with a brachytic phenotype. For example, a brachytic allele of a marker can be a marker allele that segregates with a brachytic phenotype.

As used herein, "allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

As used herein, "crossed" or "cross" means to produce progeny via fertilization (e.g. cells, seeds or plants) and includes crosses between plants (sexual) and self fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the $F_1$ generation. The term "BC1" refers to the second use of the recurrent parent, "BC2" refers to the third use of the recurrent parent, and so on. In some aspects, a backcross is performed repeatedly, with a progeny individual of each successive backcross generation being itself backcrossed to the same parental genotype.

As used herein, "elite line" means any line that has resulted from breeding and selection for superior agronomic performance. Similarly, an "elite germplasm" or elite strain of germplasm is an agronomically superior germplasm. Numerous elite lines are available and known to those of skill in the art of corn breeding.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. The term genotype can also refer to determining the genetic constitution of an individual (or group of individuals) at one or more genetic loci.

As used herein, a "haplotype" is the genotype of an individual at a plurality of genetic loci. Typically, the genetic loci described by a haplotype are physically and genetically linked, e.g., in the same chromosome interval. A haplotype can also refer to a combination of SNP alleles located within a single gene.

As used herein, the terms "phenotype," or "phenotypic trait" or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. Genetics, 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for corn, e.g., the UMC 98 map, the Nested Association Mapping (NAM) map, the Intermated B73/Mo17 (IBM2) genetic map, and the LHRF Gnp2004 map. See maizegdb.org/data_center/ map for more. All markers are used to define a specific locus in corn genomes. Large numbers of these markers have been mapped. See maizegdb.org/data_center/marker. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in corn. In some aspects, markers used herein exhibit LOD scores of 2 or greater, 3 or greater, 4 or greater, 5 or greater, 6 or greater, 7 or greater, 8 or greater, or 9 or greater with an associated trait of interest (e.g., brachysm), measuring using a method known in the art such as Qgene Version 2.23 (1996) and default parameters.

As used herein, a "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

As used herein, a "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the disclosure be limited to any particular mapping populations, use of any particular software, or any particular set of software parameters to determine linkage of a particular marker or haplotypes with a desired phenotype. It is well within the ability of one of ordinary skill in the art to extrapolate the novel features described herein to any gene pool or population of interest, and using any particular software and software parameters. Indeed, observations regarding genetic markers and haplotypes in populations in addition to those described herein are readily made using the teaching of the present disclosure. In some aspects, genetic distances referred herein are calculated from recombination values using the Kosambi function (Kosambi, The estimation of map distances from recombination values. *Annals of Eugenics,* 12:172-75 (1944)).

As used herein, "selecting" or "selection" in the context of marker-assisted selection or breeding refers to the act of picking or choosing desired individuals, normally from a population, based on certain pre-determined criteria.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a poly-nucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants" or "plant population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., *Z. mays* L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

As used herein, a "landrace" refers to a dynamic population of a cultivated plant that has historical origin, distinct identity and lacks formal crop improvement, as well as often being genetically diverse, locally adapted and associated with traditional farming systems. See Camacho Villa et al., *Plant Genetic Resources: Characterization and Utilization* 3(3):373-84 (2006).

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, "single gene converted" or "single gene conversion" refers to plants that are developed using a plant breeding technique known as backcrossing, or via genetic engineering, wherein essentially all of the desired morphological and physiological characteristics of a variety are recovered in addition to the single gene transferred into the variety via the backcrossing technique or via genetic engineering.

Brachytic corn mutants show a short stature due to a shortening of the internode length without a corresponding reduction in the number of internodes or the number and size of other organs, including the leaves, ear and tassel. See Pilu et al., *Molecular Breeding*, 20:83-91(2007). Three brachytic mutants brachytic1 (br1), brachytic2 (br2) and brachytic3 (br3) have been isolated. A maize brachytic mutant of particular agronomic potential is the recessive mutation br2, which results in the shortening of the internodes of the lower stalk with no obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with GAs, auxins, brassinosteroids and cytokinins, suggesting that the biosynthesis of these hormones is not modified by the br2 mutation. Multani et al. identified the genomic sequence of the Br2 gene and deposited it under GenBank Accession No. AY366085. See *Science*, 302(5642) 81-84 (2003). Br2 was annotated to encode a putative protein similar to adenosine triphosphate (ATP)-binding cassette transporters of the multidrug resistant (MDR) class of P-glycoproteins (PGPs).

Brachytic, dwarf, or semi-dwarf corn disclosed herein may have characteristics that make it suitable for grain and forage production, especially, production in short-season environments. In particular, the limited heat units in short-season environments reduce grain yield and lessen the probability of the crop reaching physiological maturity in a given year. The disclosed brachytic, dwarf, or semi-dwarf corn plants require fewer heat units (e.g., required 10%) than conventional hybrids to reach anthesis and generally reach physiological maturity earlier than conventional cultivars. Like semi-dwarf wheat, sorghum, and rice, corn plants disclosed herein are less prone to stalk and root lodging due to the shorter stalks and lower ear placement. Corn plants disclosed herein also has the potential to produce high-quality forage due to its high ear-to-stover ratio.

Furthermore, the altered plant structure and reduced per plant leaf area of the disclosed brachytic, dwarf, or semi-dwarf corn allow for higher planting densities to maximize grain and forage yield. Conventional corn cultivars are commonly planted at 80,000 to 90,000 plants per hectare with row spacing of 0.76 m apart. In contrast, corn plants disclosed herein can be grown as small grains with narrower rows of about 0.25 m apart with a planting density of up to 200,000 plants per hectare. Corn planting density affects light condition which in turn impacts plant growth rate. Therefore, corn plants disclosed herein provide excellent group structure, sufficient exposure to sunlight and high grain yield. Production of the corn disclosed herein at such high plant population densities further provides agroecological benefits such as reduced weed pressure, surface runoff, and evapotranspiration. For example, shorter plants with fewer and shorter leaves are more adapted to water stress than taller plants at a high planting density. Further, corn plants provided herein perform better compared to conventional corn under low nitrogen condition and have higher tolerance to reduced light.

Pilu et al. previously reported a br2-23 allele having an 8-bp deletion in the 3' end of the Br2 gene and asserted a direct relationship between this deletion and the brachytic phenotype in their br2-23 plants. See Pilu et al., *Molecular Breeding*, 20:83-91(2007). The 8-bp deletion starts at position 4148 in the Br2 mRNA sequence based on the AY366085 genomic sequence reference. Without the 8-bp deletion, the Br2 (PGP1) protein has amino acid residues N-G-W (Asparagine-Glycine-Tryptophan) from the affected codons. Although the 8-bp deletion causes a frame shift, the new sequence still codes for a N (Asparagine) and followed by G-W (Glycine-Tryptophan). Contrary to what Pilu et al described, the 8-bp deletion in BR2P_v1 panel is not concordant with the brachytic phenotype. This suggests that there is no direct relationship between the 8-bp deletion alone and the brachytic phenotype. Nevertheless, this disclosure contemplates genotyping of the 8-bp deletion together with one or more markers disclosed herein which are associated with a brachytic trait.

In one aspect, this disclosure provides methods of selecting a corn plant or seed, which methods comprise (a) providing a population of corn plants or seeds; (b) detecting in the population a corn plant or seed comprising a brachytic allele at a polymorphic locus, wherein the polymorphic locus is associated with a marker selected from the group consisting of SEQ ID Nos: 1-22 and 86-109; and (c) selecting the corn plant or seed comprising the brachytic allele. In some aspects, these methods comprise detecting a brachytic allele at a polymorphic locus within about 20 cM, 10 cM, 5 cM, 1 cM, 0.5 cM, or less than 0.5 cM of the marker selected from the group consisting of SEQ ID Nos: 1-22 and 86-109. In other aspects, these methods comprise detecting a brachytic allele of a marker selected from the group consisting of SEQ ID Nos: 1-22 and 86-109. In some aspects, these methods comprise detecting a brachytic allele at a polymorphic locus within about 20 cM, 10 cM, 5 cM, 1 cM, 0.5 cM, or less than 0.5 cM of the marker selected from the group consisting of SEQ ID Nos: 5-8, 11-22, and 86-95. In some aspects, these methods comprise detecting a brachytic allele of a marker selected from the group consisting of SEQ ID Nos: 5-8, 9-22, and 86-95. In some aspects, these methods comprise detecting a brachytic allele of a marker selected from the group consisting of SEQ ID Nos: 7 and 95. In some aspects, these methods comprise detecting a brachytic allele at a polymorphic locus in linkage disequilibrium with a marker selected from the group consisting of SEQ ID Nos: 1-22 and 86-109, and exhibits a LOD score of 2 or greater, 3 or greater, 4 or greater, 5 or greater, 6 or greater, 7 or greater, 8 or greater, or 9 or greater. In some aspects, step (a) of these methods comprises crossing a first corn plant comprising the brachytic allele with a second corn plant to produce the population of corn plants. In other aspects, step (a) further comprises backcrossing with the second corn plant. In some aspects, these methods select a corn plant or seed from a segregating population or a haploid breeding population. In other aspects, these methods select a corn plant or seed from one or more landraces. In some aspects, these landraces originate from North America, Mexico, or Italy. In some aspects, step (b) of these methods comprises using a marker assay provided herein. In some aspects, step (b) of these methods comprises the use of one or more primers selected from the group consisting of SEQ ID Nos: 23 and 24. In other aspects, step (b) of these methods comprises the use of one or more probes selected from the group consisting of SEQ ID Nos: 25 and 26. In another aspect, this disclosure provides methods of selecting a corn plant or seed, which methods comprise (a) detecting in a population of corn plants or seeds a corn plant or seed comprising a brachytic allele at a polymorphic locus, wherein the polymorphic locus is associated with a marker selected from the group consisting of SEQ ID Nos: 1-22 and 86-109; and (b) selecting the corn plant or seed comprising the brachytic allele. In other aspects, these methods further comprise genotyping the population of corn plants or seeds at one or more polymorphic sequences selected from the group consisting of SEQ ID Nos: 71-75. In further aspects, these methods further comprise detecting a brachytic allele of a marker selected from the group consisting of SEQ ID Nos: 71-75. In some aspects, the detected brachytic allele is selected from the group consisting of SEQ ID Nos: 76-80.

In another aspect, this disclosure provides methods of selecting a corn plant or seed, which methods comprise: (a) genotyping a population of corn plants or seeds at a polymorphic locus associated with a marker selected from the group consisting of SEQ ID Nos: 1-22 and 86-109; and (b) selecting a corn plant or seed comprising a brachytic allele at said polymorphic locus. In some aspects, these methods comprise genotyping at a polymorphic locus within about 20 cM, 10 cM, 5 cM, 1 cM, 0.5 cM, or less than 0.5 cM of the marker selected from the group consisting of SEQ ID Nos: 1-22 and 86-109. In other aspects, these methods comprise genotyping a marker selected from the group consisting of SEQ ID Nos: 1-22 and 86-109. In some aspects, these methods comprise genotyping a locus for at least one brachytic allele within about 20 cM, 10 cM, 5 cM, 1 cM, 0.5 cM, or less than 0.5 cM of the marker selected from the group consisting of SEQ ID Nos: 5-8, 11-22, and 86-95. In some aspects, these methods comprise genotyping a locus for at least one brachytic allele of a marker selected from the group consisting of SEQ ID Nos: 5-8, 11-22, and 86-95. In some aspects, these methods comprise genotyping a locus for at least one brachytic allele of a marker selected from the group consisting of SEQ ID Nos: 7 and 95. In some aspects, a plant or seed selected by these methods comprises a brachytic allele selected from the group consisting of SEQ ID Nos: 27-48. In other aspects, these methods further comprise genotyping the population of corn plants or seeds at one or more polymorphic sequences selected from the group consisting of SEQ ID Nos: 71-75. In some aspects, step (a) of these methods further comprise genotyping the first population of corn plants at one or more polymorphic sequences selected from the group consisting of SEQ ID Nos: 71-75. In further aspects, step (a) of these methods further comprise genotyping the first population of corn plants for a brachytic allele selected from the group consisting of SEQ ID Nos: 76-80.

In some aspects, corn plants or seeds selected using the above methods are homozygous for the brachytic allele. In other aspects, corn plants or seeds selected using these methods are heterozygous for the brachytic allele. In some aspects, corn plants or seeds selected using these methods are inbreds. In some aspects, corn plants or seeds selected using these methods are hybrids. In other aspects, corn plants or seeds selected using these methods are in an agronomically elite background. In some aspects, corn plants or seeds selected using these methods provide dwarf, semi-dwarf, or brachytic plants. In some aspects, corn plants or seeds selected using these methods have a single gene conversion of the Br2 genomic region. In some aspects, the corn plants or seeds comprise a reduced level of Br2 mRNA or protein compared to a control plant not having the brachytic allele. In other aspects, the corn plants or seeds comprise reduced Br2 protein activity compared to a control plant not having the brachytic allele. In some aspects, the height of the selected plant at maturity is reduced for about 10%, 20%, 30%, 40%, 50%, 60%, or 70% compared to a control plant not having the brachytic allele. In other aspects, the yield of the selected plant is equal to or more than the yield of a control plant not having the brachytic allele. In some aspects, corn plants or seeds selected using these methods require about 5%, 10%, 15%, 20%, or 25% fewer heat units than control plants to reach anthesis. In other aspects, corn plants or seeds selected using these methods have a relative maturity of about 10%, 15%, 20%, 25%, 30%, 35%, 40%, or 45% fewer days than the relative maturity of control plants.

In one aspect, this disclosure provides methods of creating a population of corn plants comprising at least one allele associated with a brachytic trait, the method comprising the steps of (a) genotyping a first population of corn plants, the population containing at least one allele associated with a brachytic trait, wherein the at least one brachytic allele is associated with a marker selected from the group consisting of SEQ ID Nos: 1-22 and 86-109; (b) selecting from the first population one or more corn plants containing the at least one brachytic allele; and (c) producing from the selected corn plants a second population, thereby creating a population of corn plants comprising at least one brachytic allele. In some aspects, these methods comprise genotyping a locus for at least one brachytic allele within about 20 cM, 10 cM, 5 cM, 1 cM, 0.5 cM, or less than 0.5 cM of the marker selected from the group consisting of SEQ ID Nos: 1-22 and 86-109. In other aspects, these methods comprise genotyping a marker selected from the group consisting of SEQ ID Nos: 1-22 and 86-109. In some aspects, these methods comprise genotyping a locus within about 20 cM, 10 cM, 5 cM, 1 cM, 0.5 cM, or less than 0.5 cM of the marker selected from the group consisting of SEQ ID Nos: 5-8, 11-22, and 86-95. In some aspects, these methods comprise genotyping a locus selected from the group consisting of SEQ ID Nos: 5-8, 11-22, and 86-95. In some aspects, these methods comprise genotyping a locus selected from the group consisting of SEQ ID Nos: 7 and 95. In some aspects, these methods comprise detecting a brachytic allele at a polymorphic locus in linkage disequilibrium with a marker selected from the group consisting of SEQ ID Nos: 1-22 and 86-109, and exhibits a LOD score of 2 or greater, 3 or greater, 4 or greater, 5 or greater, 6 or greater, 7 or greater, 8 or greater, or 9 or greater. In some aspects, these methods comprise genotyping a segregating population or a haploid breeding population. In some aspects, step (a) of these methods comprises using a marker assay provided herein. In some aspects, step (a) of these methods comprises the use of one or more primers selected from the group consisting of SEQ ID Nos: 23 and 24. In other aspects, step (a) of these methods comprises the use of one or more probes selected from the group consisting of SEQ ID Nos: 25 and 26. In some aspects, the population of corn plants produced by these methods are homozygous for the brachytic allele. In other aspects, the population of corn plants produced by these methods are heterozygous for the brachytic allele. In some aspects, the population of corn plants produced by these methods are inbreds. In some aspects, the population of corn plants produced by these methods are hybrids. In other aspects, the population of corn plants produced by these methods are in an agronomically elite background. In some aspects, the population of corn plants produced by these methods provide dwarf, semi-dwarf, or brachytic plants. In some aspects, the population of corn plants produced by these methods have a single gene conversion of the Br2 genomic region. In some aspects, the corn plants produced by these methods comprise a reduced level of Br2 mRNA or protein compared to a control plant not having the brachytic allele. In other aspects, the corn plants produced by these methods comprise reduced Br2 protein activity compared to a control plant not having the brachytic allele. In some aspects, the height of the produced plant at maturity is reduced for about 10%, 20%, 30%, 40%, 50%, 60%, or 70% compared to a control plant not having the brachytic allele. In other aspects, the yield of the produced plant is equal to or more than the yield of a control plant not having the brachytic allele. In some aspects, corn plants produced by these methods require about 5%, 10%, 15%, 20%, or 25% fewer heat units than control plants to reach anthesis. In other aspects, corn plants produced by these methods have a relative maturity of about 10%, 15%, 20%, 25%, 30%, 35%, 40%, or 45% fewer days than the relative maturity of control plants.

In one aspect, this disclosure provides methods of selecting a corn plant or seed, the method comprising: (a) isolating a nucleic acid from a corn plant or seed; (b) analyzing the nucleic acid to detect a polymorphic marker associated with a brachytic haplotype, the brachytic haplotype comprises one or more, two or more, three or more, four or more, five or more, six or more, seven or more, or eight or more brachytic alleles of markers selected from the group consisting of SEQ ID Nos: 1-22 and 86-109; and (c) selecting a corn plant or seed comprising the brachytic haplotype. In some aspects, these methods comprise detecting a polymorphic marker within about 20 cM, 10 cM, 5 cM, 1 cM, 0.5 cM, or less than 0.5 cM of the brachytic haplotype. In other aspects, these methods comprise detecting a brachytic haplotype comprising one or more, two or more, three or more, four or more, five or more, six or more, seven or more, or eight or more brachytic alleles of markers selected from the group consisting of SEQ ID Nos: 1-22 and 86-109. In some aspects, these methods comprise genotyping both loci SEQ ID Nos: 7 and 95. In some aspects, step (b) of these methods further comprise analyzing the nucleic acid to detect one or more polymorphic sequences selected from the group consisting of SEQ ID Nos: 71-75. In further aspects, these methods further comprise analyzing the nucleic acid to detect one or more brachytic alleles selected from the group consisting of SEQ ID Nos: 76-80.

In one aspect, this disclosure provides methods of introgressing a brachytic trait into a corn variety, the method comprising: (a) crossing a first corn variety comprising a brachytic trait with a second corn variety not comprising the brachytic trait to produce one or more progeny corn plants; (b) analyzing the one or more progeny corn plants to detect a brachytic allele, wherein the brachytic allele is linked to a marker selected from the group consisting of SEQ ID Nos: 1-22 and 86-109; and (c) selecting a progeny corn plant comprising the brachytic allele. In some aspects, these methods comprise detecting a brachytic allele within about 20 cM, 10 cM, 5 cM, 1 cM, 0.5 cM, or less than 0.5 cM of the marker selected from the group consisting of SEQ ID Nos: 1-22 and 86-109 and 71-75. In other aspects, these methods comprise detecting a brachytic allele of a marker selected from the group consisting of SEQ ID Nos: 1-22 and 86-109 and 71-75.

In another aspect, this disclosure provides hybrid brachytic, dwarf, or semi-dwarf corn plants, or plant part thereof, comprising a brachytic allele characterizable by one or more sequences selected from the group consisting of SEQ ID Nos: 27-48. In some aspects, corn plants provided herein are elite lines. In some aspects, elite corn plants provided herein are homozygous for the brachytic allele. In other aspects, elite corn plants provided herein are heterozygous for the brachytic allele. In some aspects, elite corn plants provided herein are inbreds. In some aspects, elite corn plants provided herein are hybrids. In other aspects, elite corn plants provided herein are transgenic. In some aspects, elite corn plants provided herein require about 5%, 10%, 15%, 20%, or 25% fewer heat units than control plants to reach anthesis. In other aspects, elite corn plants provided herein have a relative maturity of about 10%, 15%, 20%, 25%, 30%, 35%, 40%, or 45% fewer days than the relative maturity of control plants. In some aspects, elite corn plants provided herein have a single gene conversion of the Br2 genomic region. In some aspects, elite corn plants provided herein comprise a reduced level of Br2 mRNA or protein compared to a control plant not having the brachytic allele. In other aspects, elite corn plants provided herein comprise reduced Br2 protein activity compared to a control plant not having the brachytic allele. In some aspects, the height of elite corn plants provided herein at maturity is reduced for about 10%, 20%, 30%, 40%, 50%, 60%, or 70% compared to a control plant not having the brachytic allele. In other aspects, the yield of elite corn plants provided herein is equal to or more than the yield of a control plant not having the brachytic allele.

In one aspect, this disclosure provides a container of elite corn seeds comprising a brachytic allele characterizable by one or more sequences selected from the group consisting of SEQ ID Nos: 27-48. In a further aspect, this disclosure provides a container of transgenic elite corn seeds comprising a brachytic allele characterizable by one or more sequences selected from the group consisting of SEQ ID Nos: 27-48. In some aspects, these transgenic seeds are hybrid seeds. A container of corn seeds of the instant disclosure may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of corn seeds may be any container available in the art. By way of non-limiting example, a container may be a box, a bag, a packet, a pouch, a tape roll, a tube, or a bottle.

In one aspect, corn seeds disclosed herein can be subjected to various treatments. For example, the seeds can be treated to improve germination by priming the seeds or by disinfection to protect against seedborne pathogens. In another aspect, seeds can be coated with any available coating to improve, for example, plantability, seed emergence, and protection against seedborne pathogens. Seed coating can be any form of seed coating including, but not limited to, pelleting, film coating, and encrustments. In some aspects, corn plants or methods disclosed herein are used in combination with one or more pesticides including, but not limited to, herbicides, fungicides, insecticides, microbiocides, nematicides, insect repellents, bactericides, and other substances used to control pests. In other aspects, the corn plants or methods disclosed herein are used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

In one aspect, this disclosure provides corn plant cells, tissues, and organs that are not reproductive material and do not mediate the natural reproduction of the plant. In another aspect, this disclosure also provides corn plant cells, tissues, and organs that are reproductive material and mediate the natural reproduction of the plant. In another aspect, this disclosure provides corn plant cells, tissues, and organs that cannot maintain themselves via photosynthesis. In another aspect, this disclosure provides somatic corn plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, vascular tissue. In another aspect, this disclosure provides a corn plant chloroplast. In a further aspect, this disclosure provides epidermal cells, stomata cell, leaf or root hairs, a storage root, or a tuber. In another aspect, this disclosure provides a corn protoplast.

Skilled artisans understand that corn plants naturally reproduce via seeds, not via asexual reproduction or vegetative propagation. In one aspect, this disclosure provides corn endosperm. In another aspect, this disclosure provides corn endosperm cells. In a further aspect, this disclosure provides a male or female sterile corn plant, which cannot reproduce without human intervention.

In one aspect, corn plants disclosed herein are selected from the subspecies *Zea mays* L. ssp. *mays*. In an additional aspect, corn plants disclosed herein are selected from the group *Zea mays* L. subsp. *mays* Indentata, otherwise known as dent corn. In another aspect, corn plants disclosed herein are selected from the group *Zea mays* L. subsp. *mays* Indurata, otherwise known as flint corn. In an aspect, corn plants disclosed herein are selected from the group *Zea mays* L. subsp. *mays* Saccharata, otherwise known as sweet corn. In another aspect, corn plants disclosed herein are selected from the group *Zea mays* L. subsp. *mays* Amylacea, otherwise known as flour corn. In a further aspect, corn plants disclosed herein are selected from the group *Zea mays* L. subsp. *mays* Everta, otherwise known as pop corn. Plants disclosed herein also include hybrids, inbreds, partial inbreds, or members of defined or undefined populations.

In a further aspect, this disclosure provides processed products made from the disclosed corn plants. Such products include, but are not limited to, meal, oil, plant extract, starch, or fermentation or digestion products. In another aspect, this disclosure also provides a corn meal, which is substantially oil free and which is produced using the oilseed of any of the plants disclosed herein. In another aspect, this disclosure also provides a method of providing a corn meal by crushing oilseed of any of the plants disclosed herein.

Various corn lines disclosed herein can be used to transmit a brachytic allele disclosed here to new varieties using various cross pollination and selection methods. Breeders can also obtain hybrids using corn plants described here. Using standard crossing, backcrossing, and selection techniques, those of skill in the art may obtain commercial corn varieties with various desirable traits besides dwarfism. For example, breeders may obtain commercial dwarf corn lines and additional traits such as high nutrient use efficiency, new herbicide tolerance, increased yield, insect control, fungal disease resistance, virus resistance, nematode resistance, bacterial disease resistance, high oil production, high protein production, germination and seedling growth control, enhanced animal and human nutrition, environmental stress resistance (e.g., drought stress), increased digestibility, production of industrial enzymes, production of pharmaceutical proteins, production of pharmaceutical peptides, production of pharmaceutical small molecules, improved processing traits, improved flavor, improved hybrid seed production, reduced allergenicity, improved production of biopolymers or biofuels, and cytoplasmic male sterility.

Corn plants or lines disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes that modify oil content, genes that control male sterility, genes that affect abiotic stress resistance, and other genes and transcription factors that affect plant growth and agronomic traits such as yield, flowering, plant growth or plant structure.

Corn Transformation

Corn plants disclosed herein can also be genetically transformed. Numerous methods for plant transformation have been developed including biological and physical plant transformation protocols. See, for example, Mild, et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

One method for introducing an expression vector into plants is based on the natural transformation system of *Agrobacterium*. See e.g., Horsch, et al., *Science* 227:1229 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by. for example. U.S. Pat. No. 5,563,055 (Townsend and Thomas), incorporated herein by reference in its entirety.

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of a selectable marker gene allows for preferential selection of transformed cells, tissues and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

Corn plants or seeds disclosed herein can also be produced by one or more genome engineering techniques or subject to further genomic editing. For example, one or more brachytic alleles can be introduced into a non-brachytic background. Exemplary genome engineering techniques include meganucleases, Zinc-Finger nuclease, TALENs, and CRISPR-cas9 system. See, e.g., Gaj et al., *Trends in Biotechnology*, 31(7):397-405 (2013).

Additional Breeding

Corn plants disclosed herein can also be subject to additional breeding using one or more known methods in the art, e.g., pedigree breeding, recurrent selection, mass selection, and mutation breeding. Pedigree breeding starts with the crossing of two genotypes, such as a corn variety comprising a brachytic allele disclosed herein and another corn variety lacking such a allele. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety may be crossed with another variety to produce a first generation progeny plant. The first generation progeny plant may then be backcrossed to one of its parent varieties to create a BC1 or BC2. Progeny plants are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation breeding can also be used to introduce new traits into corn plants disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques.

In some aspects, the instant disclosure provides doubled haploid corn plants and seeds that comprise a brachytic trait or brachytic marker alleles. The doubled haploid (DH) approach achieves isogenic plants in a shorter time frame, and is particularly useful for generating inbred lines and quantitative genetics studies. DH plants can be produced according to methods known in the art. For example, the initial step involves the haploidization of the plant which results in the production of a population comprising haploid seed. Non-homozygous lines are crossed with an inducer parent, resulting in the production of haploid seeds. Seeds that have haploid embryos, but normal triploid endosperm, advance to the second stage. After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid testcross production.

The present disclosure also provides production of hybrid seeds comprising one or more brachytic alleles disclosed here and exhibit a brachytic, dwarf, or semi-dwarf phenotype. The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in corn, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved corn lines that may be used as inbreds for hybrid production. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, either through visual or molecular methods.

Marker Detection

The present disclosure also provides novel polymorphic markers from the Br2 genomic region which can be used to select for brachytic corn plants. Exemplary polymorphic markers are shown in Tables 2 and 7 with their brachytic alleles listed. Markers within approximately 20 cM, 10 cM, 5 cM, 1 cM, 0.5 cM, or less than 0.5 cM of these exemplary markers can also be identified from the known art and used in the methods disclosed herein.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

Herein, nucleic acid analysis methods include, but are not limited to, PCR-based detection methods, microarray methods, mass spectrometry-based methods and/or nucleic acid sequencing methods. In one aspect, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant or seed, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain aspects, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another aspect, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, *Science* 311:1544-46 (2006).

In alternative aspects, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Any of the aforementioned marker types can be employed in the context of the disclosure to identify brachytic alleles or brachytic haplotypes associated with brachysm.

The markers to be used in the methods of the present disclosure should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

In some aspects, corn genotyping, including SNP detection disclosed herein can be via high throughput, non-destructive seed sampling. In some aspects, haploid seed is sampled in this manner and only seed with at least one marker genotype of interest is advanced for doubling. Apparatus and methods for the high-throughput, non-destructive sampling of seeds have been described which would overcome the obstacles of statistical samples by allowing for individual seed analysis. For example, U.S. patent application Ser. No. 11/213,430 (filed Aug. 26, 2005); U.S. patent application Ser. No. 11/213,431 (filed Aug. 26, 2005); U.S. patent application Ser. No. 11/213,432 (filed Aug. 26, 2005); U.S. patent application Ser. No. 11/213,434 (filed Aug. 26, 2005); and U.S. patent application Ser. No. 11/213,435 (filed Aug. 26, 2005), U.S. patent application Ser. No. 11/680,611 (filed Mar. 2, 2007), which are incorporated herein by reference in their entirety, disclose apparatus and systems for the automated sampling of seeds as well as methods of sampling, testing and bulking seeds.

Association Mapping

In one aspect, the present disclosure also provides haplotypes, marker loci, germplasm for conducting genome-wide association mapping. Exemplary marker loci and brachytic alleles are listed in Table 2. Genome-wide association mapping is conducted to find signals of association for various complex traits by surveying genetic variation in the whole genome. Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, (2002) pp. 59-68).

An approach used to link phenotypic variation with genetic loci is marker-trait association (MTA) mapping, also known as linkage disequilibrium (LD) mapping. LD mapping emerged as an important gene mapping tool in early 1990's with the advent of high-throughput genotyping technology, and has been widely used in human genetics to identify genes affecting human diseases. This approach was introduced and began to be adopted in plant gene mapping studies in early 2000's (Flint-Garcia et al. (2003) *Annu Rev Plant Biol* 54: 357-374).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al. (2001) *Nature*

411:199-204). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., F2, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTL

In some aspects, markers, alleles, and haplotypes provided herein can be used for identifying QTLs associated with corn plant height and plant architecture. The statistical principles of QTL identification include penalized regression analysis, ridge regression, single point marker analysis, complex pedigree analysis, Bayesian MCMC, identity-by-descent analysis, interval mapping, composite interval mapping (CIM), and Haseman-Elston regression.

SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander and Botstein, *Genetics,* 121:185-199 (1989), and the interval mapping, based on maximum likelihood methods described by Lander and Botstein, *Genetics,* 121:185-199 (1989), and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, *Genetics,* 121:185-199 (1989), and further described by Arús and Moreno-González, *Plant Breeding,* Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, *Genetics,* 139:1421-1428 (1995), the entirety of which is herein incorporated by reference). Multiple regression methods or models can be also be used, in which the trait is regressed on a large number of markers (Jansen, *Biometrics in Plant Breed,* van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding,* Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, *Genetics,* 136:1447-1455 (1994) and Zeng, *Genetics,* 136:1457-1468 (1994). Generally, the use of cofactors reduces the bias and sampling error of the estimated QTL positions (Utz and Melchinger, *Biometrics in Plant Breeding,* van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, *Genetics,* 136:1457-1468 (1994)). These models can be extended to multi-environment experiments to analyze genotype-environment interactions (Jansen et al., *Theo. Appl. Genet.* 91:33-37 (1995).

The compositions and methods of the present disclosure can be utilized to guide MAS or breeding corn varieties with a desired complement (set) of allelic forms of associated with superior agronomic performance (e.g. brachysm or dwarfism). Any of the disclosed marker alleles can be introduced into a corn line via introgression, by traditional breeding (or introduced via transformation, or both) to yield a corn plant with superior agronomic performance.

These marker loci can be introgressed into any desired genomic background, germplasm, plant, line, variety, etc., as part of an overall MAS breeding program designed to improve corn architecture and enhance corn yield.

The present disclosure also extends to a method of making a progeny corn plant and the resulting progeny corn plants. In one aspect, the method comprises crossing a first parent corn plant with a second corn plant and growing the corn plant parent under plant growth conditions to yield corn plant progeny. Methods of crossing and growing corn plants are well within the ability of those of ordinary skill in the art. Such corn plant progeny can be assayed for brachytic alleles as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants may be a corn plant of the present disclosure in that it comprises at least one of the allelic forms of the markers of the present disclosure, such that the progeny are capable of inheriting the allele.

Marker Assisted Selection (MAS) Breeding

Polymorphic markers and their brachytic alleles provided herein can be used in MAS breeding of brachytic corn. In some aspects, polymorphic markers disclosed herein are within the coding sequence of a causative gene. They are ideal for MAS as no recombination is expected between them and the sequence of DNA responsible for the phenotype. Markers do not need to contain or correspond to causal mutations in order to be effective in MAS.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that harbor a brachytic allele and therefore are brachytic or can give rise to brachytic plants.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In some aspects, a first corn plant or germplasm exhibiting a desired trait (the donor, e.g., a brachytic corn) can be crossed with a second corn plant or germplasm (the recipient, e.g., an elite or exotic corn, depending on characteristics that are desired in the progeny) to create an introgressed corn plant or germplasm as part of a breeding program. In some aspects, the recipient plant can also contain one or more loci associated with one or more desired traits, which can be qualitative or quantitative trait loci. In another aspect, the recipient plant can contain a transgene.

In some aspects, the recipient corn plant or germplasm will typically lack desired traits as compared to the first corn plant or germplasm, while the introgressed corn plant or germplasm will display improved traits as compared to the second plant or germplasm. An introgressed corn plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

Introgression of a Brachytic Trait Using MAS

The instant disclosure provides methods and markers for introgressing a brachytic trait into a new corn variety using MAS. Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with a brachytic trait are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to the brachytic trait and can also be made based on the recurrent parent genotype, wherein screening is performed on a genetic marker and/or phenotype basis. In another aspect, markers of this disclosure can be used in conjunction with other markers, ideally at least one on each chromosome of the corn genome, to track the introgression of the brachytic trait into elite germplasm. It is within the scope of this disclosure to utilize the methods and compositions for integration of a brachytic trait. It is contemplated by the inventors that the present disclosure will be useful for developing commercial varieties with a brachytic trait and other agronomically elite phenotypes.

Listed below are exemplary embodiments of the instant disclosure.

Embodiment 1

A method for selecting a corn plant or seed, said method comprising:
 a. detecting in a population of corn plants or seeds a corn plant or seed comprising a brachytic allele at a polymorphic locus, wherein said polymorphic locus is associated with a marker selected from the group consisting of SEQ ID Nos: 1-22 and 86-109; and
 b. selecting said corn plant or seed comprising said brachytic allele.

Embodiment 2

The method of Embodiment 1, wherein said polymorphic locus is within about 20 cM, 10 cM, 5 cM, 1 cM, 0.5 cM, or less than 0.5 cM of said marker selected from the group consisting of SEQ ID Nos: 1-22 and 86-109.

Embodiment 3

The method of Embodiment 1, wherein said polymorphic locus is selected from the group consisting of SEQ ID Nos: 1-22 and 86-109.

Embodiment 4

The method of Embodiment 1, wherein said polymorphic locus is in linkage disequilibrium with said marker selected from the group consisting of SEQ ID Nos: 1-22 and 86-109, and exhibits a LOD score of 2 or greater, 3 or greater, 4 or greater, 5 or greater, 6 or greater, 7 or greater, 8 or greater, or 9 or greater.

Embodiment 5

The method of Embodiment 1, wherein said method comprises crossing a first corn plant comprising said brachytic allele with a second corn plant to produce said population of corn plants or seeds.

Embodiment 6

The method of Embodiment 5, wherein said method further comprises backcrossing with said second corn plant.

Embodiment 7

The method of Embodiment 1, wherein said population of corn plants or seeds is a segregating population.

Embodiment 8

The method of Embodiment 1, wherein said population of corn plants or seeds is a haploid breeding population.

Embodiment 9

The method of Embodiment 1, wherein said step (a) comprises a marker assay.

Embodiment 10

The method of Embodiment 1, wherein said step (a) comprises the use of one or more primers selected from the group consisting of SEQ ID Nos: 23 and 24.

Embodiment 11

The method of Embodiment 1, wherein said step (a) comprises the use of one or more probes selected from the group consisting of SEQ ID Nos: 25 and 26.

Embodiment 12

The method of Embodiment 1, wherein said selected plant or seed is homozygous for said brachytic allele.

Embodiment 13

The method of Embodiment 1, wherein said selected plant or seed is heterozygous for said brachytic allele.

Embodiment 14

The method of Embodiment 1, wherein said selected plant or seed is an inbred.

Embodiment 15

The method of Embodiment 1, wherein said selected plant or seed is a hybrid.

Embodiment 16

The method of Embodiment 1, wherein said selected plant or seed is in an agronomically elite background.

Embodiment 17

The method of Embodiment 1, wherein said selected plant is dwarf.

Embodiment 18

The method of Embodiment 1, wherein said selected plant is semi-dwarf.

Embodiment 19

The method of Embodiment 1, wherein said selected plant is brachytic.

Embodiment 20

The method of Embodiment 1, wherein said selected plant or seed comprising a single gene conversion of the Br2 genomic region.

Embodiment 21

The method of Embodiment 1, wherein said population of corn plants or seeds are from one or more landraces.

Embodiment 22

The method of Embodiment 1, wherein said selected plant or seed comprises a reduced level of Br2 mRNA or protein compared to a control plant not having said brachytic allele.

Embodiment 23

The method of Embodiment 1, wherein said selected plant or seed comprises reduced Br2 protein activity compared to a control plant not having said brachytic allele.

Embodiment 24

The method of Embodiment 1, wherein the height of said selected plant at maturity is reduced for about 10%, 20%, 30%, 40%, 50%, 60%, or 70% compared to a control plant not having said brachytic allele.

Embodiment 25

The method of Embodiment 1, wherein the yield of said selected plant is equal to or more than the yield of a control plant not having said brachytic allele.

Embodiment 26

The method of Embodiment 1, wherein said selected plant requires about 5%, 10%, 15%, 20%, or 25% fewer heat units than a control non-brachytic plant to reach anthesis.

Embodiment 27

The method of Embodiment 1, wherein said selected plant has a relative maturity of about 10%, 15%, 20%, 25%, 30%, 35%, 40%, or 45% fewer days than the relative maturity of a control non-brachytic plant.

Embodiment 28

The method of Embodiment 1, wherein said brachytic allele predicts a brachytic trait with a accuracy of at least about 50%, 60%, 70%, 75%, 80%, 85%, 90%, 95%, 99%, or 100%.

Embodiment 29

A method for selecting a corn plant or seed, said method comprising:
a. genotyping a population of corn plants or seeds at a polymorphic locus associated with a marker selected from the group consisting of SEQ ID Nos: 1-22 and 86-109; and b. selecting a corn plant or seed comprising a brachytic allele at said polymorphic locus.

Embodiment 30

The method of Embodiment 29, wherein said polymorphic locus is within about 20 cM, 10 cM, 5 cM, 1 cM, 0.5 cM, or less than 0.5 cM of said marker selected from the group consisting of SEQ ID Nos: 1-22 and 86-109.

Embodiment 31

The method of Embodiment 29, wherein said polymorphic locus is selected from the group consisting of SEQ ID Nos: 1-22 and 86-109.

Embodiment 32

A method of creating a population of corn plants comprising at least one allele associated with a brachytic trait, said method comprising the steps of:
  a. genotyping a first population of corn plants, said population containing at least one allele associated with a brachytic trait, wherein said at least one brachytic allele is associated with a marker selected from the group consisting of SEQ ID Nos: 1-22 and 86-109;
  b. selecting from said first population one or more corn plants containing said at least one brachytic allele; and
  c. producing from said selected corn plants a second population, thereby creating a population of corn plants comprising said at least one brachytic allele.

Embodiment 33

The method of Embodiment 32, wherein said at least one brachytic allele is within about 20 cM, 10 cM, 5 cM, 1 cM, 0.5 cM, or less than 0.5 cM of said marker selected from the group consisting of SEQ ID Nos: 1-22 and 86-109.

Embodiment 34

The method of Embodiment 32, wherein said at least one brachytic allele is at a marker selected from the group consisting of SEQ ID Nos: 1-22 and 86-109.

Embodiment 35

A method for selecting a corn plant or seed, said method comprising:
  a. isolating a nucleic acid from a corn plant or seed;
  b. analyzing said nucleic acid to detect a polymorphic marker associated with a brachytic haplotype, said brachytic haplotype comprises one or more, two or more, three or more, four or more, five or more, six or more, seven or more, or eight or more brachytic alleles of markers selected from the group consisting of SEQ ID Nos: 1-22 and 86-109; and
  c. selecting a corn plant or seed comprising said brachytic haplotype.

Embodiment 36

The method of Embodiment 35, wherein said polymorphic marker is within about 20 cM, 10 cM, 5 cM, 1 cM, 0.5 cM, or less than 0.5 cM of said brachytic haplotype.

Embodiment 37

The method of Embodiment 35, wherein said polymorphic marker is selected from the group consisting of SEQ ID Nos: 1-22 and 86-109.

Embodiment 38

A method for introgressing a brachytic trait into a corn variety, said method comprising:
  a. crossing a first corn variety comprising a brachytic trait with a second corn variety not comprising said brachytic trait to produce one or more progeny corn plants;
  b. analyzing said one or more progeny corn plants to detect a brachytic allele, wherein said brachytic allele is linked to a marker selected from the group consisting of SEQ ID Nos: 1-22 and 86-109; and
  c. selecting a progeny corn plant comprising said brachytic allele.

Embodiment 39

The method of Embodiment 38, wherein said brachytic allele is within about 20 cM, 10 cM, 5 cM, 1 cM, 0.5 cM, or less than 0.5 cM of said marker selected from the group consisting of SEQ ID Nos: 1-22 and 86-109.

Embodiment 40

The method of Embodiment 39, wherein said brachytic allele is at said marker selected from the group consisting of SEQ ID Nos: 1-22 and 86-109.

Embodiment 41

The method of Embodiment 39, further comprising:
  d. crossing said selected progeny plant with itself or with said second corn plant to produce one or more further progeny corn plants; and
  e. selecting a further progeny plant comprising said brachytic allele.

Embodiment 42

The method of Embodiment 41, wherein step (e) of selecting comprises marker-assisted selection.

Embodiment 43

A hybrid dwarf or semi-dwarf corn variety, or a plant part thereof, comprising a brachytic allele characterizable by one or more sequences selected from the group consisting of SEQ ID Nos: 27-48.

Embodiment 44

The hybrid dwarf or semi-dwarf corn variety, or a plant part thereof, of claim 43, wherein said variety is homozygous for said brachytic allele.

Embodiment 45

The hybrid dwarf or semi-dwarf corn variety, or a plant part thereof, of claim 43, wherein said variety is transgenic.

Embodiment 46

The method of Embodiment 1, wherein said method further comprises genotyping said population of corn plants or seeds at one or more polymorphic sequences selected from the group consisting of SEQ ID Nos: 71-75.

Embodiment 47

The method of Embodiment 1, wherein said step (a) further comprising detecting a brachytic allele at a polymorphic locus selected from the group consisting of SEQ ID Nos: 71-75.

Embodiment 48

The method of Embodiment 29, wherein said method further comprises genotyping said population of corn plants or seeds at one or more polymorphic sequences selected from the group consisting of SEQ ID Nos: 71-75.

Embodiment 49

The method of Embodiment 29, wherein said method further comprises selecting a corn plant or seed comprising a brachytic allele selected from the group consisting of SEQ ID Nos: 76-80.

Embodiment 50

The method of Embodiment 32, wherein said method further comprises genotyping said first population of corn plants at one or more polymorphic sequences selected from the group consisting of SEQ ID Nos: 71-75.

Embodiment 51

The method of Embodiment 32, wherein step (a) of said method further comprising genotyping for at least one brachytic allele selected from the group consisting of SEQ ID Nos: 76-80.

Embodiment 52

The method of Embodiment 35, wherein said method further comprises analyzing said nucleic acid to detect one or more polymorphic sequences selected from the group consisting of SEQ ID Nos: 71-75.

Embodiment 53

The method of Embodiment 35, wherein step (b) of said method further comprising analyzing said nucleic acid to detect at least one brachytic allele selected from the group consisting of SEQ ID Nos: 76-80.

EXAMPLES

Example 1. Sequencing of the Br2 Genomic Region in a Panel of Both Brachytic and Non-Brachytic Plants Targeted sequencing of the Br2 genomic region is conducted in a collection of 23 proprietary maize inbred lines (Table 1). This collection of lines is hereafter referred to as the BR2P_v1 panel. The panel comprises four brachytic lines from North America, six brachytic lines from Mexico, two brachytic lines from Italy, and one brachytic line with an unknown origin. Both the North American and Mexican inbred lines are derived from a brachytic germplasm source which originated from Brazil. The Italian inbred lines come from an independent European brachytic germplasm source. The panel also comprises ten non-brachytic lines from these same regions for comparison.

Multani et al. identified the genomic sequence of the Br2 gene and deposited it under GenBank Accession No. AY366085. See *Science*, 302(5642)81-84 (2003). Br2 was annotated to encode a putative protein similar to adenosine triphosphate (ATP)-binding cassette transporters of the multidrug resistant (MDR) class of P-glycoproteins (PGPs). Internal contig sequences from the genomic region containing the Br2 gene are analyzed and designated as Mon B73 in Table 1.

To sequence the Br2 genomic region, 16 sets of primers are designed through alignment of Mon B73 sequence of the Br2 gene using DNAStar. These primers can amplify the entire Br2 genomic gene including a 1 kb upstream flanking sequence and a 2 kb downstream flanking sequence (about 11,000 bp in total). PCR amplification is performed using genomic DNA extracted from each line in the BR2P_v1 panel. PCR thermocycling conditions include 30 seconds at 98° C., 35 cycles of 5 seconds at 98° C., 5 seconds of 60° C., 15 seconds of 72° C., 1.0 minute at 72° C. For a 50 µl volume of PCR reaction, 10 ng/µl of genomic DNA, 10 µM of each primer (forward and reverse), and 1× Phire Hot Start II DNA Polymerase PCR Mix (Thermo Scientific) are used. PCR products are then cleaned up with ExoSap protocol (Affymetrix) and submitted for Sanger sequencing. Sequence Contigs are assembled using SeqMan Pro into complete Br2 genomic sequences for the subsequent polymorphism identification.

TABLE 1

Reference lines and the BR2P_v1 panel used for targeted sequencing of the Br2 (PGP1) genomic region

| Sample ID | Origin | Brachytic Status | Gender | Panel |
|---|---|---|---|---|
| MON_B73 | na | BR2* | not applicable | Reference |
| AY366085_B73 | na | BR2 | not applicable | Reference |
| MPL1 | North America | br2** | F | BR2P_v1 |
| MPL2 | North America | br2 | M | BR2P_v1 |
| MPL3 | North America | br2 | F | BR2P_v1 |
| MPL4 | North America | br2 | M | BR2P_v1 |
| MPL5 | Mexico | br2 | F | BR2P_v1 |
| MPL6 | Mexico | br2 | M | BR2P_v1 |
| MPL7 | Mexico | br2 | F | BR2P_v1 |
| MPL8 | Mexico | br2 | F | BR2P_v1 |
| MPL9 | Mexico | br2 | M | BR2P_v1 |
| MPL10 | Mexico | br2 | M | BR2P_v1 |
| MPL11 | Italy | br2 | F | BR2P_v1 |
| MPL12 | Italy | br2 | M | BR2P_v1 |
| MPL13 | na† | br2 | na | BR2P_v1 |
| I294213 | North America | BR2 | F | BR2P_v1 |
| I285291 | North America | BR2 | M | BR2P_v1 |
| CV995128 | North America | BR2 | F | BR2P_v1 |
| CV760185 | North America | BR2 | M | BR2P_v1 |
| MPL14 | Mexico | BR2 | F | BR2P_v1 |
| MPL15 | Mexico | BR2 | F | BR2P_v1 |
| MPL16 | Mexico | BR2 | M | BR2P_v1 |
| MPL17 | Mexico | BR2 | M | BR2P_v1 |

TABLE 1-continued

Reference lines and the BR2P_v1 panel used for
targeted sequencing of the Br2 (PGP1) genomic region

| Sample ID | Origin | Brachytic Status | Gender | Panel |
|---|---|---|---|---|
| MPL18 | Italy | BR2 | M | BR2P_v1 |
| MPL19 | Italy | BR2 | F | BR2P_v1 |

*BR2: non-brachytic phenotype;
**br2: brachytic phenotype;
†na: not available;
I294213 (see U.S. Pat. No. 7,166,779);
I285291 (see U.S. Pat. No. 7,211,717);
CV995128 (see U.S. Pat. No. 8,319,066);
CV760185 (see U.S. Pat. No. 8,581,076);
"Gender" denotes which way the line is used in hybrid make-up combinations; M (Male); F (Female).

Example 2. Identification of New Br2 Polymorphisms

In addition to the Br2 genomic region, sequence data are also collected from the BR2P_v1 panel for a downstream region of the Br2 gene. Sequence polymorphisms are identified base on the Br2 genomic and downstream sequences obtained from the BR2P_v1 panel. In total, 190 polymorphisms are identified including both SNPs and INDELs. A polymorphism is defined as a difference in the DNA sequence between any of the 23 sequenced lines compared to the reference sequence (MON_B73 or AY366085) or between any of the lines compared to each other in the BR2P_v1 panel. Depending on the location of the polymorphism, any amino acid changes resulted from the polymorphisms are also determined.

The 190 identified polymorphisms are analyzed for their concordance with the brachytic phenotype. Among them, polymorphisms shown in SEQ ID Nos: 1-22 are fully concordant with the brachytic phenotype in the Mexican and North American lines in the BR2P_v1 panel (Table 2). Concordance is defined as all brachytic lines from Mexico and North America have one allele from the listed polymorphisms and all other lines have a different allele.

Pilu et al. previously reported a br2-23 allele having an 8-bp deletion in the 3' end of the Br2 gene and asserted a direct relationship between this deletion and the brachytic phenotype in their br2-23 plants. See Pilu et al., *Molecular Breeding*, 20:83-91(2007); see also, Cassani et al., *Plant Growth Regul.*, 64(2):185-92 (2011). The same 8-bp deletion is present in the BR2P_v1 panel, which is designated as "the 8-bp deletion" here. The 8-bp deletion starts at position 4148 in the Br2 mRNA sequence based on the AY366085 genomic sequence reference. Without the 8-bp deletion, the Br2 (PGP1) protein has amino acid residues N-G-W (Asparagine-Glycine-Tryptophan) from the affected codons. Although the 8-bp deletion causes a frame shift, the new sequence still codes for a N (Asparagine) and followed by G-W (Glycine-Tryptophan). This is because the deleted 8-bp sequence is part of a small tetranucleotide repeat, resulting in repeated amino acid residues in the protein. Due to the frame shift, the 8-bp deletion is predicted to lead to the removal of three amino acids from the translated Br2 protein. However, it is unclear what impact, if any, the missing amino acids may have on Br2 protein functions.

Contrary to what Pilu et al. described, the 8-bp deletion in BR2P_v1 panel is not concordant with the brachytic phenotype. This deletion is however concordant with the non-brachytic male lines that originate from North America, Mexico, and Italy (highlighted with bold text in Table 3). This suggests that there is no direct relationship between the 8-bp deletion alone and the brachytic phenotype.

TABLE 2

Polymorphisms concordant with the brachytic phenotype.

| Marker (SEQ ID) | Start* | Polymorphism Position* | End* | Sample Brachytic Allele | Sample Brachytic Allele (SEQ ID) | Sample Non-Brachytic Allele | Sample Non-Brachytic Allele (SEQ ID) | Polymorphism Type | AY366085 Position | Br2 Exon/Intron | mRNA Position |
|---|---|---|---|---|---|---|---|---|---|---|---|
| 1 | 202337238 | 202337309 | 202337380 | T | 27 | G | 49 | SNP | 2375 | Intron3 | na |
| 2 | 202337242 | 202337213 | 202337384 | T | 28 | G | 50 | SNP | 2379 | Intron3 | na |
| 3 | 202337247 | 202337218 | 202337389 | G | 29 | A | 51 | SNP | 2384 | Intron3 | na |
| 4 | 202337248 | 202337219-202337222 | 202337393 | — | 30 | TATA | 52 | INDEL | 2385-2388 | Intron3 | na |
| 5 | 202337294 | 202337363-202337365 | 202337436 | — | 31 | GAA | 53 | INDEL | 2429-2431 | Intron3 | na |
| 6 | 202337299 | 202337368 | 202337439 | G | 32 | A | 54 | SNP | 2434 | Intron3 | na |
| 7 | 202337336 | 202337407 | 202337478 | T | 33 | G | 55 | SNP | 2473 | Exon4 | 1560 |
| 8 | 202337562 | 202337633-202337638 | 202337705 | GTCCGT | 34 | — | 56 | INDEL | 2698-2699 | Intron4 | na |
| 9 | 202337578 | 202337643-202337644 | 202337713 | GG | 35 | — | 57 | INDEL | 2708-2709 | Intron4 | na |
| 10 | 202337582 | 202337645-202337646 | 202337717 | TA | 36 | — | 58 | INDEL | 2710-2711 | Intron4 | na |
| 11 | 202337587 | 202337648 | 202337719 | A | 37 | C | 59 | SNP | 2714 | Intron4 | na |
| 12 | 202343446 | 202343515 | 202343586 | T | 38 | C | 60 | SNP | na | downstream of Br2 | na |
| 13 | 202343474 | 202343545 | 202343616 | T | 39 | G | 61 | SNP | na | downstream of Br2 | na |
| 14 | 202343637 | 202343708 | 202343779 | G | 40 | A | 62 | SNP | na | downstream of Br2 | na |
| 15 | 202343694 | 202343765 | 202343836 | G | 41 | C | 63 | SNP | na | downstream of Br2 | na |
| 16 | 202343695 | 202343766 | 202343837 | A | 42 | C | 64 | SNP | na | downstream of Br2 | na |
| 17 | 202343696 | 202343767 | 202343838 | C | 43 | T | 65 | SNP | na | downstream of Br2 | na |

TABLE 2-continued

Polymorphisms concordant with the brachytic phenotype.

| Marker (SEQ ID) | Start* | Polymorphism Position* | End* | Sample Brachytic Allele | Sample Brachytic Allele (SEQ ID) | Sample Non-Brachytic Allele | Sample Non-Brachytic Allele (SEQ ID) | Polymorphism Type | AY366085 Position | Br2 Exon/Intron | mRNA Position |
|---|---|---|---|---|---|---|---|---|---|---|---|
| 18 | 202343697 | 202343768 | 202343839 | G | 44 | C | 66 | SNP | na | downstream of Br2 | na |
| 19 | 202343698 | 202343769 | 202343840 | C | 45 | G | 67 | SNP | na | downstream of Br2 | na |
| 20 | 202343700 | 202343771 | 202343842 | T | 46 | A | 68 | SNP | na | downstream of Br2 | na |
| 21 | 202343701 | 202343772 | 202343843 | C | 47 | A | 69 | SNP | na | downstream of Br2 | na |
| 22 | 202343702 | 202343773-202343776 | 202343847 | CTCG | 48 | — | 70 | INDEL | na | downstream of Br2 | na |

*Physical Position on Public B73 RefGen_v3 Map (bp);
SNP = single nucleotide polymorphism;
INDEL = insertion deletion polymorphism;
bp = base pair of Arizona Genomics Institute B73 RefGen_v3 sequence;
na: not available

TABLE 3

A survey of the 8-bp deletion in the BR2P_v1 panel.

| Sample ID | 8-bp deletion | Brachytic_Status |
|---|---|---|
| MON_B73 | no deletion | BR2 |
| AY366085 | no deletion | BR2 |
| MPL1 | no deletion | br2 |
| MPL2 | no deletion | br2 |
| MPL3 | no deletion | br2 |
| MPL4 | no deletion | br2 |
| MPL5 | no deletion | br2 |
| MPL6 | no deletion | br2 |
| MPL7 | no deletion | br2 |
| MPL8 | no deletion | br2 |
| MPL9 | no deletion | br2 |
| MPL10 | no deletion | br2 |
| MPL11 | no deletion | br2 |
| MPL12 | no deletion | br2 |
| MPL13 | no deletion | br2 |
| I294213 | no deletion | BR2 |
| I285291 | deletion | BR2 |
| CV995128 | no deletion | BR2 |
| CV760185 | deletion | BR2 |
| MPL14 | no deletion | BR2 |
| MPL15 | no deletion | BR2 |
| MPL16 | deletion | BR2 |
| MPL17 | deletion | BR2 |
| MPL18 | deletion | BR2 |
| MPL19 | no deletion | BR2 |

Example 3. Predictive Power of the Polymorphic Marker SEQ ID 7

SEQ ID 7 provides a single nucleotide polymorphism (SNP) in Br2 Exon 4 having a brachytic allele (the T allele) and a non-brachytic allele (the G allele). This SNP is at position 1560 of the mRNA sequence for Br2 (PGP1) based on AY366085 and corresponds to the $520^{th}$ amino acid residue of the protein. This SNP results in a synonymous substitution as both alleles provide a codon for a Leucine (Table 4).

Mexican and North American lines with brachytic phenotype in the BR2P_v1 panel carry a brachytic allele of SEQ ID 7 (the T allele). The non-brachytic lines carry a non-brachytic allele (the G allele). The brachytic trait is recessive. The association between SEQ ID 7 and brachysm was further tested with additional corn varieties not present in the BR2P_v1 panel. SEQ ID 7 is 100% accurate for predicting brachysm in North American lines (n=20) and 98% accurate in Mexican lines (n=47). SEQ ID 7 is 50% accurate for predicting brachysm in Italian lines (n=14) (Table 5). These results show that SEQ ID 7 is highly associated with the brachytic trait in Mexican and North American lines, but less so in Italian lines.

TABLE 4

Primers and probes for detecting polymorphism SEQ ID 7.

| SEQ ID | Chromosome | Forward Primer (SEQ ID) | Reverse Primer (SEQ ID) | br2 Probe (SEQ ID) | Br2 Probe (SEQ ID) |
|---|---|---|---|---|---|
| 7 | 1 | GATGAAGTCTGCAATTCGGTTTTGG (SEQ ID 23) | GCTCACCAGCCCGATCTG (SEQ ID 24) | CCGTCCAGAAGGATT (SEQ ID 25) | CGTCCAGCAGGATT (SEQ ID 26) |

T = brachytic (br2); G = non-brachytic (Br2)

Example 4. Intron Splicing Analysis

SEQ ID 7 has been validated on a panel of brachytic and non-brachytic material from Mexico and found to be 96% predictive of the brachytic phenotype. Since several non-brachytic Mexican lines in the validation panel are genotyped with the brachytic TT allele, there are likely additional polymorphisms with functional effects on the brachytic trait in those lines. The other 10 polymorphisms that are fully concordant with the brachytic phenotype in the BR2P_v1 panel are located in Intron 3 and Intron 4. This suggests that these polymorphisms may impact intron/exon splice junctions and thus alter mRNA processing.

VISTA-Point (available at webpage pipeline.lbl.gov/cgi-bin/gateway2) is used to find islands of intronic conservation in pairwise comparisons within monocots. Splice site motifs, branch points, and conserved regions of the PGP1 gene based on AY366085 sequence are identified. Marker SEQ ID 8 contains a 5'-GTCCGT-3' insertion at the start of Intron 4 and at the last nucleotide of a putative splice site. This insertion sequence includes the consensus splice site nucleotides "GTNNGT" (Reddy et al., *Annu. Rev. Plant Biol.* 58:267-94(2007)). The proximity of this insertion to the 3' end of Exon 4 and to the likely splice site indicates a high probability of functionality.

TABLE 5

Characterization of SEQ ID 7 accuracy.

| | # of Lines | |
|---|---|---|
| North America | | |
| Brachytic | 10 | |
| Non-Brachytic | 10 | |
| | Brachytic | Non-Brachytic |
| TT | 10 | 0 |
| GG | 0 | 10 |
| False Positive | 0% | |
| False Negative | 0% | |
| Overall Accuracy | 100% | |
| (10 + 10)/(10 + 10) × 100% = 100% | | |
| Mexico | | |
| Brachytic | 39 | |
| Non-Brachytic | 8 | |
| | Brachytic | Non-Brachytic |
| TT | 38 | 1 |
| GG | 0 | 8 |
| False Positive | 2% | |
| False Negative | 0% | |
| Overall Accuracy | 98% | |
| (38 + 8)/(39 + 8) × 100% = 98% | | |
| Italy | | |
| Brachytic | 8 | |
| Non-Brachytic | 6 | |
| | Brachytic | Non-Brachytic |
| TT | 1 | 0 |
| GG | 7 | 6 |
| False Positive | 0% | |
| False Negative | 50% | |
| Overall Accuracy | 50% | |
| (1 + 6)/(8 + 6) × 100% = 50% | | |

TABLE 6

Further validation of SEQ ID 7 accuracy for predicting the brachytic trait in lines of north America or Mexico origin.

| | # of Lines | |
|---|---|---|
| North America | | |
| Brachytic | 49 | |
| Non-Brachytic | 69 | |
| | Brachytic | Non-Brachytic |
| TT | 49 | 0 |
| TG | 0 | 0 |
| GG | 0 | 69 |
| Missing | 0 | 0 |
| False Positive | 0% | |
| False Negative | 0% | |
| Overall Accuracy | 100% | |
| (49 + 69)/(49 + 69) × 100% = 100% | | |
| Mexico | | |
| Brachytic | 41 | |
| Non-Brachytic | 242 | |
| | Brachytic | Non-Brachytic |
| TT | 41 | 11 |
| TG | 0 | 1 |
| GG | 0 | 223 |
| Missing | 0 | 7 |
| False Positive | 5% | |
| False Negative | 0% | |
| Overall Accuracy | 96% | |
| (41 + 223)/(41 + 242 − 7) × 100% = 96% | | |

Example 5. Introgression of a Br2 Brachytic Allele to Produce a New Brachytic Variety A corn plant comprising a brachytic allele disclosed herein is crossed with another non-brachytic corn line comprising a desirable trait (e.g., improved yield under drought, cold, heat stress conditions). $F_1$ progeny plants from this cross is assayed for one or more SNP markers exemplified in Table 2 to select for the brachytic allele. A selected $F_1$ progeny plant is then backcrossed with the parent non-brachytic corn line comprising the desirable trait (recurrent parent). Plants from the BC1 generation are also genotyped using SNP markers exemplified in Table 2 to select for the brachytic allele. After multiple rounds of backcrossing (e.g., 5-7 generations), a new brachytic corn line is obtained comprising the desirable trait in the recurrent parent elite line.

Example 6. Additional Br2 Polymorphisms in Exon 5

Additional Br2 polymorphisms are identified in exon 5 of the Br2 coding sequence. These polymorphic sequences are listed in Table 7. Markers are developed from these polymorphisms and are used to monitor a brachytic trait by themselves or in combination with one or more polymorphisms listed in Table 2.

TABLE 7

Additional polymorphisms identified in exon 5 of the Br2 coding sequence.

| Marker (SEQ ID) | Sample Brachytic Allele | Sample Brachytic Allele (SEQ ID) | Sample Non-Brachytic Allele | Sample Non-Brachytic Allele (SEQ ID) | Polymorphism Type | AY366085 Position[1] | Br2 Exon/Intron | mRNA Position[2] |
|---|---|---|---|---|---|---|---|---|
| 71 | A | 76 | C | 81 | SNP | 4505 | Exon 5 | 1992 |
| 72 | G | 77 | C | 82 | SNP | 4985 | Exon 5 | 2472 |
| 73 | C | 78 | A | 83 | SNP | 5027 | Exon 5 | 2514 |
| 74 | T | 79 | G | 84 | SNP | 5245 | Exon 5 | 2732 |
| 75 | G | 80 | C | 85 | SNP | 5306 | Exon 5 | 2793 |

[1]Genomic position on AY366085, starting with the first nucleotide of the coding region and including introns.
[2]mRNA position starting with the first nucleotide of the coding region and not including introns.

Example 7. Additional Br2 Polymorphisms and Markers for Mexican and North American Lines Further sequencing of the BR2P_v1 panel in Table 1 reveals more Br2 polymorphic sequences and also provides updated sequence information for polymorphisms identified previously. These new polymorphic sequences and markers, including their exemplary brachytic and non-brachytic alleles are listed in Table 8. Table 8's polymorphisms are fully concordant with the brachytic phenotype in the Mexican and North American lines in the BR2P_v1 panel.

TABLE 8

Polymorphisms concordant with the brachytic phenotype in Mexican and North American lines.

| Marker (SEQ ID) | Start* | Polymorphism Position* | End* | Sample Brachytic Allele | Sample Non-Brachytic Allele | Polymorphism Type | AY366085 Position | Br2 Exon/Intron | mRNA Position |
|---|---|---|---|---|---|---|---|---|---|
| 86 | 202337238 | 202337309-202337314 | 202337380 | — | GATAGA | INDEL | 2375-2380 | Intron3 | na |
| 87 | 202337248 | 202337222-202337223 | 202337393 | TG | — | INDEL | 2388-2389 | Intron3 | na |
| 88 | 202337578 | 202337643-202337646 | 202337717 | GGTA | — | INDEL | 2708-2711 | Intron4 | na |
| 89 | 202337815 | 202337885-202337890 | 202337960 | — | GTTGTT | INDEL | 2951-2956 | Intron4 | na |
| 90 | 202337815 | 202337891 | 202337960 | T | G | SNP | 2957 | Intron4 | na |
| 91 | 202337953 | 202338011-202338012 | 202338055 | TT | — | INDEL | 3077-3078 | Intron4 | na |
| 92 | 202340996 | 202341061-202341062 | 202341127 | multi-kilobase insertion (SEQ ID No. 111) | — | INDEL | 6127-6128 | Exon5 | 3551-3552 |
| 93 | 202339026 | 202339076-202339160 | 202339210 | — | TTGCCAAGCAATGCTCGCATGCCCATGCATGCATCATCCCTGGTCAAACTCAAACACTCTCCACCGTCAGGGAATAAGACTTATT (SEQ ID No. 118) | INDEL | 4143-4227 | Intron4 | na |
| 94 | 202339136 | 202339186-202339187 | 202339257 | AACAATTCCATTTTTATT (SEQ ID No. 117) | — | INDEL | 4253-4254 | Intron4 | na |

*Physical Position on Public B73 RefGen_v3 Map (bp); SNP = single nucleotide polymorphism; INDEL = insertion deletion polymorphism; bp = base pair of Arizona Genomics Institute B73 RefGen_v3 sequence; na: not available

TABLE 9

Polymorphic markers in Italian lines.

| Marker (SEQ ID) | Start* | Poly-morphism Position* | End* | Sample Brachytic Allele | Sample Non-Brachytic Allele | Poly-morphism Type | Br2 AY366085 Position | Exon/ Intron | mRNA Position |
|---|---|---|---|---|---|---|---|---|---|
| 95 | 202338059 | 202338124-202338125 | 202338190 | 579-bp insertion (SEQ ID No. 110) | — | INDEL | 3190-3191 | Intron4 | na |
| 96 | 202334500 | 202334566 | 202334600 | — | CCTGGAACGGGTG (SEQ ID No. 119) | INDEL | na | 5'UTR | na |
| 97 | 202336808 | 202336878 | 202336948 | T | A | SNP | 1944 | Intron3 | na |
| 98 | 202336808 | 202336880 | 202336948 | C | T | SNP | 1946 | Intron3 | na |
| 99 | 202337082 | 202337152-202337153 | 202337223 | — | GC | INDEL | 2218-2219 | Intron3 | na |
| 100 | 202338733 | 202338802 | 202338870 | A | C | SNP | 3869 | Intron4 | na |
| 101 | 202338798 | 202338866-202338867 | 202338938 | — | T | INDEL | 3933-3944 | Intron4 | na |
| 102 | 202338885 | 202338954 | 202339025 | G | T | SNP | 4021 | Intron4 | na |
| 103 | 202338937 | 202339007 | 202339077 | C | GC | SNP | 4074 | Intron4 | na |
| 104 | 202338991 | 202339061-202339062 | 202339132 | — | T | INDEL | 4128-4129 | Intron4 | na |
| 105 | 202339107 | 202339177 | 202339247 | A | C | SNP | 4244 | Intron4 | na |
| 106 | 202339128 | 202339198 | 202339268 | T | G | SNP | 4265 | Intron4 | na |
| 107 | 202339145 | 202339215 | 202339283 | G | A | SNP | 4282 | Intron4 | na |
| 108 | 202339217 | 202339283-202339284 | 202339349 | — | T | INDEL | 4350-4351 | Intron4 | na |
| 109 | 202343667 | 202343730-202343731 | 202343797 | — | GCCGTGCCGA (SEQ ID No. 120) | INDEL | na | | |

*Physical Position on Public B73 RefGen_v3 Map (bp); SNP = single nucleotide polymorphism; INDEL = insertion deletion polymorphism; bp = base pair of Arizona Genomics Institute B73 RefGen_v3 sequence; na: not available Among these new markers, SEQ ID Nos: 86 and 87 reside in the same region as SEQ ID Nos: 1 to 4 and provide updated sequences for the previous four polymorphic markers. SEQ ID No: 88 represents a consolidation of the polymorphisms in SEQ ID Nos: 9 and 10.

Example 8. Additional Br2 Polymorphisms and Markers for Italian Lines

Further sequencing of additional Italian brachytic lines provides a new Br2 polymorphic marker (SEQ ID No: 95, Table 9) concordant with the brachytic phenotype in Italian lines of the BR2P_v1 panel from Table 1. This marker is unique to brachytic lines of Italian origin. A non-brachytic allele of SEQ ID No: 95 comprises a 579-bp insertion.

Additional polymorphisms (SEQ ID Nos: 96 to 109, Table 9) are also identified in Italian brachytic lines (Table 9). Surprisingly, these markers though appear unique to Italian brachytic lines, the brachytic alleles appear identical to reference B73 (non-brachytic) sequences.

Marker selection accuracy is estimated for SEQ ID No: 95. Among 34 Italian lines being genotyped at SEQ ID No: 95, 8 lines are brachytic and the other 26 lines are non-brachytic. Seven out of 8 brachytic lines carry the 579-bp insertion (brachytic allele, the insertion sequence is shown in SEQ ID No. 110), while none of the 26 non-brachytic lines carries such an insertion. Therefore, overall prediction accuracy is 97% (Table 10). Exemplary primer and probe sequences used to genotype marker SEQ ID No: 95 are listed in Table 11.

TABLE 10

Characterization of SEQ ID No. 95 maker accuracy for Italian lines.

| All Italian Lines | Total Number of Lines tested | Carrying 579-bp Insertion |
|---|---|---|
| Brachytic | 8 | 7 |
| Non-Brachytic | 26 | 0 |
| False Positive | | 0% |
| False Negative | | 13% |
| Overall Accuracy | | 97% |
| (7 + 26)/(8 + 26) × 100% = 97% | | |

TABLE 11

Primers and probes for detecting polymorphism SEQ ID No. 95.

| SEQ ID | Chromosome | Forward Primer | Reverse Primer | Non-brachytic Br2 Probe | Brachytic br2 Probe |
|---|---|---|---|---|---|
| 95 | 1 | CATCCGTTCCA CTCCACTCAC (SEQ ID No: 112) | ATCTGAGGCTAGCTA CTAAAGCTTTAGC (SEQ ID No: 113, for amplifying non-brachytic polymorphism) TGGAGGCCAAGTATA TCCTGGAT (SEQ ID No: 114, located in 579-bp insertion and for amplifying brachytic polymorphism) | TCATGCGTC GCGCACT (SEQ ID No: 115) | AGGCCCGT ATATGGC (SEQ ID No: 116) |

As various modifications could be made in the constructions and methods herein described and illustrated without departing from the scope of the disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method for selecting a corn plant or seed, said method comprising:
   a) crossing a first corn plant comprising a brachytic allele at a polymorphic locus with a second corn plant to produce a population of progeny corn plants or progeny seeds
   b) conducting a marker assay to detect in said progeny population of corn plants or progeny seeds a progeny corn plant or progeny seed comprising said brachytic allele at a polymorphic locus, wherein said B polymorphic locus comprises SEQ ID NO: 7 having a thymidine (T) at position 72; and
   c) selecting said progeny corn plant or progeny seed comprising said brachytic allele.

2. The method of claim 1, wherein said polymorphic locus is within 20 cM of SEQ ID NO: 7.

3. The method of claim 1, wherein said polymorphic locus is SEQ ID NO: 7.

4. The method of claim 1, wherein said method further comprises backcrossing said selected progeny corn plant or a corn plant grown from said selected progeny seed with said second corn plant.

5. The method of claim 1, wherein said step b) comprises the use of primers comprising SEQ ID NO: 23 and 24.

6. The method of claim 1, wherein said step h) comprises the use of probes comprising SEQ ID NOs: 25 and 26.

7. The method of claim 1, wherein said selected plant or seed is a hybrid.

8. The method of claim 1, wherein the height of said selected plant at maturity is reduced between 10% and 70% compared to a control plant not having said brachytic allele.

9. The method of claim 1, wherein the yield of said selected plant is equal to or more than the yield of a control plant not having said brachytic allele.

10. The method of claim 1, wherein said selected plant requires between 5% and 25% fewer heat units than a control non-brachytic plant to reach anthesis.

11. The method of claim 1, wherein said selected plant has a relative maturity of between 10% and 45% fewer days than the relative maturity of a control non-brachytic plant.

12. The method of claim 1, wherein said brachytic allele predicts a brachytic trait with an accuracy of at least 50%.

13. The method of claim 1, wherein said step b) comprises the use of primers comprising SEQ ID NOs: 112 and 113 or reverse complements thereof.

14. The method of claim 1, wherein said step b) comprises the use of primers comprising SEQ ID NOs: 112 and 114 or reverse complements thereof.

15. The method of claim 1, wherein said step b) comprises the use of probes comprising SEQ ID NOs: 115 and 116 or reverse complements thereof.

\* \* \* \* \*

SEQUENCE LISTING

<160> NUMBER OF SEQ ID NOS: 120

<210> SEQ ID NO 1
<211> LENGTH: 143
<212> TYPE: DNA
<213> ORGANISM: Zea mays
<220> FEATURE:
<221> NAME/KEY: variation
<222> LOCATION: (72)..(72)
<223> OTHER INFORMATION: n = A, T, C, G, or deletion
<220> FEATURE:
<221> NAME/KEY: misc_feature
<222> LOCATION: (72)..(72)
<223> OTHER INFORMATION: n is a, c, g, t, delection, or insertion

<400> SEQUENCE: 1
ttgcctagca catgcctgcc attgaccgac tgctcagtga gaagtggttc agttgtgctg      60
ttgacagtat anatagatat atatagtagc cctgtagatt ttttttcag acaaaaaaag     120 aagaagaacg agatgaagtc tgc                                             143

<210> SEQ ID NO 2
<211> LENGTH: 143
<212> TYPE: DNA
<213> ORGANISM: Zea mays
<220> FEATURE:
<221> NAME/KEY: variation
<222> LOCATION: (72)..(72)
<223> OTHER INFORMATION: n = A, T, C, G, or deletion
<220> FEATURE:
<221> NAME/KEY: misc_feature
<222> LOCATION: (72)..(72)
<223> OTHER INFORMATION: n is a, c, g, t, delection, or insertion

<400> SEQUENCE: 2
ctagcacatg cctgccattg accgactgct cagtgagaag tggttcagtt gtgctgttga      60
cagtatagat anatatatat agtagccctg tagattttttt tttcagacaa aaaagaaga    120 agaacgagat gaagtctgca att                                             143

<210> SEQ ID NO 3

```
<211> LENGTH: 143
<212> TYPE: DNA
<213> ORGANISM: Zea mays
<220> FEATURE:
<221> NAME/KEY: variation
<222> LOCATION: (72)..(72)
<223> OTHER INFORMATION: n = A, T, C, G, or deletion
<220> FEATURE:
<221> NAME/KEY: misc_feature
<222> LOCATION: (72)..(72)
<223> OTHER INFORMATION: n is a, c, g, t, delection, or insertion

<400> SEQUENCE: 3
acatgcctgc cattgaccga ctgctcagtg agaagtggtt cagttgtgct gttgacagta      60
tagatagata tntatagtag ccctgtagat ttttttttca gacaaaaaaa gaagaagaac     120
gagatgaagt ctgcaattcg gtt                                             143

<210> SEQ ID NO 4
<211> LENGTH: 146
<212> TYPE: DNA
<213> ORGANISM: Zea mays
<220> FEATURE:
<221> NAME/KEY: variation
<222> LOCATION: (72)..(75)
<223> OTHER INFORMATION: n = A, T, C, G, or deletion
<220> FEATURE:
<221> NAME/KEY: misc_feature
<222> LOCATION: (72)..(75)
<223> OTHER INFORMATION: n is a, c, g, t, delection, or insertion

<400> SEQUENCE: 4
catgcctgcc attgaccgac tgctcagtga gaagtggttc agttgtgctg ttgacagtat      60
agatagatat annnngtagc cctgtagatt ttttttttcag acaaaaaaag aagaagaacg    120
agatgaagtc tgcaattcgg ttttgg                                          146

<210> SEQ ID NO 5
<211> LENGTH: 143
<212> TYPE: DNA
<213> ORGANISM: Zea mays
<220> FEATURE:
<221> NAME/KEY: variation
<222> LOCATION: (70)..(72)
<223> OTHER INFORMATION: n = A, T, C, G, or deletion
<220> FEATURE:
<221> NAME/KEY: misc_feature
<222> LOCATION: (70)..(72)
<223> OTHER INFORMATION: n is a, c, g, t, delection, or insertion

<400> SEQUENCE: 5
gctgttgaca gtatagatag atatatatag tagccctgta gatttttttt tcagacaaaa      60
aaagaagaan nncgagatga agtctgcaat tcggttttgg cagggcaaat cctgctggac    120
gggcacgacc tcaggtcgct gga                                             143

<210> SEQ ID NO 6
<211> LENGTH: 141
<212> TYPE: DNA
<213> ORGANISM: Zea mays
<220> FEATURE:
<221> NAME/KEY: variation
<222> LOCATION: (70)..(70)
<223> OTHER INFORMATION: n = A, T, C, G, or deletion
<220> FEATURE:
<221> NAME/KEY: misc_feature
<222> LOCATION: (70)..(70)
<223> OTHER INFORMATION: n is a, c, g, t, delection, or insertion

<400> SEQUENCE: 6
```

```
tgacagtata gatagatata tatagtagcc ctgtagattt tttttcaga caaaaaaaga      60 agaagaacgn gatgaagtct gcaattcggt tttggcaggg caaatcctgc tggacgggca    120
cgacctcagg tcgctggagc t                                              141
```

<210> SEQ ID NO 7
<211> LENGTH: 143
<212> TYPE: DNA
<213> ORGANISM: Zea mays
<220> FEATURE:
<221> NAME/KEY: variation
<222> LOCATION: (72)..(72)
<223> OTHER INFORMATION: n = A, T, C, G, or deletion
<220> FEATURE:
<221> NAME/KEY: misc_feature
<222> LOCATION: (72)..(72)
<223> OTHER INFORMATION: n is a, c, g, t, delection, or insertion

<400> SEQUENCE: 7

```
tttttttttc agacaaaaaa agaagaagaa cgagatgaag tctgcaattc ggttttggca     60
gggcaaatcc tnctggacgg gcacgacctc aggtcgctgg agctgcggtg gctgcggcgg   120
cagatcgggc tggtgagcca gga                                            143
```

<210> SEQ ID NO 8
<211> LENGTH: 144
<212> TYPE: DNA
<213> ORGANISM: Zea mays
<220> FEATURE:
<221> NAME/KEY: variation
<222> LOCATION: (72)..(77)
<223> OTHER INFORMATION: n = A, T, C, G, or deletion
<220> FEATURE:
<221> NAME/KEY: misc_feature
<222> LOCATION: (72)..(77)
<223> OTHER INFORMATION: n is a, c, g, t, delection, or insertion

<400> SEQUENCE: 8

```
aggcggccag ggtggccaac gcccactcct tcatcatcaa actccccgac ggctacgaca     60
cgcaggtccg tnnnnnnccc gtatagctag ctcactagct gcactgccac ttctctcgct   120
tgctccccca ccgttgctgc ctgt                                           144
```

<210> SEQ ID NO 9
<211> LENGTH: 136
<212> TYPE: DNA
<213> ORGANISM: Zea mays
<220> FEATURE:
<221> NAME/KEY: variation
<222> LOCATION: (66)..(67)
<223> OTHER INFORMATION: n = A, T, C, G, or deletion
<220> FEATURE:
<221> NAME/KEY: misc_feature
<222> LOCATION: (66)..(67)
<223> OTHER INFORMATION: n is a, c, g, t, delection, or insertion

<400> SEQUENCE: 9

```
caacgcccac tccttcatca tcaaactccc cgacggctac gacacgcagg tccgtcccgt     60
atagcnntag ctcactagct gcactgccac ttctctcgct tgctccccca ccgttgctgc   120
ctgttgctct ccaatc                                                    136
```

<210> SEQ ID NO 10
<211> LENGTH: 136
<212> TYPE: DNA
<213> ORGANISM: Zea mays
<220> FEATURE:

```
<221> NAME/KEY: variation
<222> LOCATION: (64)..(65)
<223> OTHER INFORMATION: n = A, T, C, G, or deletion
<220> FEATURE:
<221> NAME/KEY: misc_feature
<222> LOCATION: (64)..(65)
<223> OTHER INFORMATION: n is a, c, g, t, delection, or insertion

<400> SEQUENCE: 10
gcccactcct tcatcatcaa actccccgac ggctacgaca cgcaggtccg tcccgtatag      60
ctanngctca ctagctgcac tgccacttct ctcgcttgct cccccaccgt tgctgcctgt    120
tgctctccaa tccact                                                    136

<210> SEQ ID NO 11
<211> LENGTH: 133
<212> TYPE: DNA
<213> ORGANISM: Zea mays
<220> FEATURE:
<221> NAME/KEY: variation
<222> LOCATION: (62)..(62)
<223> OTHER INFORMATION: n = A, T, C, G, or deletion
<220> FEATURE:
<221> NAME/KEY: misc_feature
<222> LOCATION: (62)..(62)
<223> OTHER INFORMATION: n is a, c, g, t, delection, or insertion

<400> SEQUENCE: 11
ctccttcatc atcaaactcc ccgacggcta cgacacgcag gtccgtcccg tatagctagc     60
tnactagctg cactgccact tctctcgctt gctcccccac cgttgctgcc tgttgctctc    120
caatccactt gtc                                                       133

<210> SEQ ID NO 12
<211> LENGTH: 141
<212> TYPE: DNA
<213> ORGANISM: Zea mays
<220> FEATURE:
<221> NAME/KEY: misc_feature
<222> LOCATION: (70)..(70)
<223> OTHER INFORMATION: n is a, c, g, t, delection, or insertion

<400> SEQUENCE: 12
cacacgcaca cacacagatc gcctgacaag ccagccattg cttcagatca agaaactgc      60 gtaataattn ctttctttct ttctttcttt ctttccagag cacaagggag ggggttata    120 atggctagta cctgactgac t                                              141

<210> SEQ ID NO 13
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, delection, or insertion

<400> SEQUENCE: 13
agccagccat tgcttcagat caaagaaact gcgtaataat tcctttcttt ctttctttct     60
ttctttccag ancacaaggg aggggggtta taatggctag tacctgactg actgtacgag    120
ccgagattaa cggcagtcac ctc                                            143

<210> SEQ ID NO 14
<211> LENGTH: 143
<212> TYPE: DNA
<213> ORGANISM: Zea mays
```

<220> FEATURE:
<221> NAME/KEY: misc_feature
<222> LOCATION: (72)..(72)
<223> OTHER INFORMATION: n is a, c, g, t, deletion, or insertion

<400> SEQUENCE: 14
atcgccctgc tggccatttg gcaccaccta gtcgtacatg tgttcagtca tttccgtcca    60
ttactactac gnccgtgctc acccgtgccg acgcgccgtg catggtcccc gtcccggctg   120
gaacgcgtcc tcggaagaga gag                                          143

<210> SEQ ID NO 15
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 15
ccattactac tacgaccgtg ctcacccgtg ccgacgcgcc gtgcatggtc cccgtcccgg    60
ctggaacgcg tnctcggaag agagagatag agcacagcag acaggagaca agggatggaa   120
ggatggcgtt cgcccggtac agg                                          143

<210> SEQ ID NO 16
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 16
cattactact acgaccgtgc tcacccgtgc cgacgcgccg tgcatggtcc ccgtcccggc    60
tggaacgcgt cntcggaaga gagagataga gcacagcaga cagggagaca gggatggaag   120
gatggcgttc gcccggtaca ggt                                          143

<210> SEQ ID NO 17
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 17
attactacta cgaccgtgct cacccgtgcc gacgcgccgt gcatggtccc cgtcccggct    60
ggaacgcgtc ncggaagag agagatagag cacagcagac agggagacag ggatggaagg   120
atggcgttcg cccggtacag gtt                                          143

<210> SEQ ID NO 18
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 18
ttactactac gaccgtgctc acccgtgccg acgcgccgtg catggtcccc gtcccggctg    60
gaacgcgtcc tnggaagaga gagatagagc acagcagaca gggagacagg gatggaagga    120
tggcgttcgc ccggtacagg ttg                                            143

<210> SEQ ID NO 19
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 19
ttactactac gaccgtgctc acccgtgccg acgcgccgtg catggtcccc gtcccggctg    60
gaacgcgtcc tnggaagaga gagatagagc acagcagaca gggagacagg gatggaagga    120
tggcgttcgc ccggtacagg ttg                                            143

<210> SEQ ID NO 20
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 20
ctactacgac cgtgctcacc cgtgccgacg cgccgtgcat ggtccccgtc ccggctggaa    60
cgcgtcctcg gnagagagag atagagcaca gcagacaggg agacagggat ggaaggatgg    120
cgttcgcccg gtacaggttg cta                                            143

<210> SEQ ID NO 21
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 21
tactacgacc gtgctcaccc gtgccgacgc cgtgcatg gtccccgtcc cggctggaac     60
gcgtcctcgg angagagaga tagagcacag cagacaggga cagggatg gaaggatggc    120 gttcgcccgg tacaggttgc tag                                            143

<210> SEQ ID NO 22
<211> LENGTH: 146
<212> TYPE: DNA
<213> ORGANISM: Zea mays
<220> FEATURE:
<221> NAME/KEY: misc_feature
<222> LOCATION: (72)..(75)
<223> OTHER INFORMATION: n is a, c, g, t, deletion, or insertion

<400> SEQUENCE: 22
actacgaccg tgctcacccg tgccgacgcg ccgtgcatgg tccccgtccc ggctggaacg    60
cgtcctcgga annnngagag agatagagca cagcagacag ggagacaggg atggaaggat    120
ggcgttcgcc cggtacaggt tgctag                                         146

<210> SEQ ID NO 23
<211> LENGTH: 25
<212> TYPE: DNA
<213> ORGANISM: Zea mays
<220> FEATURE:
<221> NAME/KEY: misc_feature
<222> LOCATION: (1)..(25)
<223> OTHER INFORMATION: primer

<400> SEQUENCE: 23
gatgaagtct gcaattcggt tttgg                                          25

<210> SEQ ID NO 24
<211> LENGTH: 18
<212> TYPE: DNA
<213> ORGANISM: Zea mays
<220> FEATURE:
<221> NAME/KEY: misc_feature
<222> LOCATION: (1)..(18)
<223> OTHER INFORMATION: primer

<400> SEQUENCE: 24
gctcaccagc ccgatctg                                                  18

<210> SEQ ID NO 25
<211> LENGTH: 15
<212> TYPE: DNA
<213> ORGANISM: Zea mays
<220> FEATURE:
<221> NAME/KEY: misc_feature
<222> LOCATION: (1)..(15)
<223> OTHER INFORMATION: probe

<400> SEQUENCE: 25
ccgtccagaa ggatt                                                     15

<210> SEQ ID NO 26
<211> LENGTH: 14
<212> TYPE: DNA
<213> ORGANISM: Zea mays
<220> FEATURE:
<221> NAME/KEY: misc_feature
<222> LOCATION: (1)..(14)
<223> OTHER INFORMATION: probe

<400> SEQUENCE: 26
cgtccagcag gatt                                                      14

<210> SEQ ID NO 27
<211> LENGTH: 143
<212> TYPE: DNA
<213> ORGANISM: Zea mays

<400> SEQUENCE: 27
ttgcctagca catgcctgcc attgaccgac tgctcagtga gaagtggttc agttgtgctg    60
ttgacagtat atatagatat atatagtagc cctgtagatt tttttttcag acaaaaaaag   120
aagaagaacg agatgaagtc tgc                                           143

<210> SEQ ID NO 28
<211> LENGTH: 143
<212> TYPE: DNA
<213> ORGANISM: Zea mays

<400> SEQUENCE: 28
ctagcacatg cctgccattg accgactgct cagtgagaag tggttcagtt gtgctgttga    60

```
cagtatagat atatatatat agtagccctg tagatttttt tttcagacaa aaaaagaaga    120
agaacgagat gaagtctgca att                                           143
```

<210> SEQ ID NO 29
<211> LENGTH: 143
<212> TYPE: DNA
<213> ORGANISM: Zea mays

<400> SEQUENCE: 29

```
acatgcctgc cattgaccga ctgctcagtg agaagtggtt cagttgtgct gttgacagta    60
tagatagata tgtatagtag ccctgtagat tttttttttca gacaaaaaaa gaagaagaac   120
gagatgaagt ctgcaattcg gtt                                           143
```

<210> SEQ ID NO 30
<211> LENGTH: 142
<212> TYPE: DNA
<213> ORGANISM: Zea mays

<400> SEQUENCE: 30

```
catgcctgcc attgaccgac tgctcagtga gaagtggttc agttgtgctg ttgacagtat    60
agatagatat agtagccctg tagatttttt tttcagacaa aaaagaaga  agaacgagat    120 gaagtctgca attcggtttt gg                                            142
```

<210> SEQ ID NO 31
<211> LENGTH: 140
<212> TYPE: DNA
<213> ORGANISM: Zea mays

<400> SEQUENCE: 31

```
gctgttgaca gtatagatag atatatatag tagccctgta gattttttttt tcagacaaaa   60 aaagaagaac gagatgaagt ctgcaattcg gttttggcag ggcaaatcct gctggacggg    120
cacgacctca ggtcgctgga                                               140
```

<210> SEQ ID NO 32
<211> LENGTH: 141
<212> TYPE: DNA
<213> ORGANISM: Zea mays

<400> SEQUENCE: 32

```
tgacagtata gatagatata tatagtagcc ctgtagattt tttttcaga  caaaaaaga    60 agaagaacgg gatgaagtct gcaattcggt tttggcaggg caaatcctgc tggacgggca    120
cgacctcagg tcgctggagc t                                             141
```

<210> SEQ ID NO 33
<211> LENGTH: 141
<212> TYPE: DNA
<213> ORGANISM: Zea mays

<400> SEQUENCE: 33

```
tgacagtata gatagatata tatagtagcc ctgtagattt tttttcaga  caaaaaaga    60 agaagaacgg gatgaagtct gcaattcggt tttggcaggg caaatcctgc tggacgggca    120
cgacctcagg tcgctggagc t                                             141
```

<210> SEQ ID NO 34
<211> LENGTH: 144
<212> TYPE: DNA
<213> ORGANISM: Zea mays

```
<400> SEQUENCE: 34
aggcggccag ggtggccaac gcccactcct tcatcatcaa actccccgac ggctacgaca    60
cgcaggtccg tgtccgtccc gtatagctag ctcactagct gcactgccac ttctctcgct   120
tgctccccca ccgttgctgc ctgt                                          144

<210> SEQ ID NO 35
<211> LENGTH: 136
<212> TYPE: DNA
<213> ORGANISM: Zea mays

<400> SEQUENCE: 35
caacgcccac tccttcatca tcaaactccc cgacggctac gacacgcagg tccgtcccgt    60
atagcggtag ctcactagct gcactgccac ttctctcgct tgctccccca ccgttgctgc   120
ctgttgctct ccaatc                                                   136

<210> SEQ ID NO 36
<211> LENGTH: 136
<212> TYPE: DNA
<213> ORGANISM: Zea mays

<400> SEQUENCE: 36
gcccactcct tcatcatcaa actccccgac ggctacgaca cgcaggtccg tcccgtatag    60
ctatagctca ctagctgcac tgccacttct ctcgcttgct cccccaccgt tgctgcctgt   120
tgctctccaa tccact                                                   136

<210> SEQ ID NO 37
<211> LENGTH: 133
<212> TYPE: DNA
<213> ORGANISM: Zea mays

<400> SEQUENCE: 37
ctccttcatc atcaaactcc ccgacggcta cgacacgcag gtccgtcccg tatagctagc    60
taactagctg cactgccact tctctcgctt gctcccccac cgttgctgcc tgttgctctc   120
caatccactt gtc                                                      133

<210> SEQ ID NO 38
<211> LENGTH: 141
<212> TYPE: DNA
<213> ORGANISM: Zea mays

<400> SEQUENCE: 38
cacacgcaca cacacagatc gcctgacaag ccagccattg cttcagatca agaaactgc     60 gtaataattt ctttctttct ttctttcttt ctttccagag cacaagggag ggggttata    120 atggctagta cctgactgac t                                             141

<210> SEQ ID NO 39
<211> LENGTH: 143
<212> TYPE: DNA
<213> ORGANISM: Zea mays

<400> SEQUENCE: 39
agccagccat tgcttcagat caaagaaact gcgtaataat tcctttcttt ctttctttct    60
ttctttccag atcacaaggg agggggttaa taatggctag tacctgactg actgtacgag   120
ccgagattaa cggcagtcac ctc                                           143
```

<210> SEQ ID NO 40
<211> LENGTH: 143
<212> TYPE: DNA
<213> ORGANISM: Zea mays

<400> SEQUENCE: 40
atcgccctgc tggccatttg gcaccaccta gtcgtacatg tgttcagtca tttccgtcca      60
ttactactac ggccgtgctc acccgtgccg acgcgccgtg catggtcccc gtcccggctg     120
gaacgcgtcc tcggaagaga gag                                             143

<210> SEQ ID NO 41
<211> LENGTH: 143
<212> TYPE: DNA
<213> ORGANISM: Zea mays

<400> SEQUENCE: 41
ccattactac tacgaccgtg ctcacccgtg ccgacgcgcc gtgcatggtc cccgtcccgg      60
ctggaacgcg tgctcggaag agagagatag agcacagcag acagggagac agggatggaa     120
ggatggcgtt cgcccggtac agg                                             143

<210> SEQ ID NO 42
<211> LENGTH: 143
<212> TYPE: DNA
<213> ORGANISM: Zea mays

<400> SEQUENCE: 42
cattactact acgaccgtgc tcacccgtgc cgacgcgccg tgcatggtcc ccgtcccggc      60
tggaacgcgt catcggaaga gagagataga gcacagcaga cagggagaca gggatggaag     120
gatggcgttc gcccggtaca ggt                                             143

<210> SEQ ID NO 43
<211> LENGTH: 143
<212> TYPE: DNA
<213> ORGANISM: Zea mays

<400> SEQUENCE: 43
attactacta cgaccgtgct cacccgtgcc gacgcgccgt gcatggtccc cgtcccggct      60
ggaacgcgtc cccggaagag agagatagag cacagcagac agggagacag ggatggaagg     120
atggcgttcg cccggtacag gtt                                             143

<210> SEQ ID NO 44
<211> LENGTH: 143
<212> TYPE: DNA
<213> ORGANISM: Zea mays

<400> SEQUENCE: 44
ttactactac gaccgtgctc acccgtgccg acgcgccgtg catggtcccc gtcccggctg      60
gaacgcgtcc tgggaagaga gagatagagc acagcagaca gggagacagg gatggaagga    120
tggcgttcgc ccggtacagg ttg                                             143

<210> SEQ ID NO 45
<211> LENGTH: 143
<212> TYPE: DNA
<213> ORGANISM: Zea mays

<400> SEQUENCE: 45
tactactacg accgtgctca cccgtgccga cgcgccgtgc atggtccccg tcccggctgg      60

```
aacgcgtcct ccgaagagag agatagagca cagcagacag ggagacaggg atggaaggat    120
ggcgttcgcc cggtacaggt tgc                                            143

<210> SEQ ID NO 46
<211> LENGTH: 143
<212> TYPE: DNA
<213> ORGANISM: Zea mays

<400> SEQUENCE: 46
ctactacgac cgtgctcacc cgtgccgacg cgccgtgcat ggtccccgtc ccggctggaa    60
cgcgtcctcg gtagagagag atagagcaca gcagacaggg agacaggat ggaaggatgg    120 cgttcgcccg gtacaggttg cta                                            143

<210> SEQ ID NO 47
<211> LENGTH: 143
<212> TYPE: DNA
<213> ORGANISM: Zea mays

<400> SEQUENCE: 47
tactacgacc gtgctcaccc gtgccgacgc gccgtgcatg gtccccgtcc cggctggaac    60
gcgtcctcgg acgagagaga tagagcacag cagacaggga gacagggatg gaaggatggc    120
gttcgcccgg tacaggttgc tag                                            143

<210> SEQ ID NO 48
<211> LENGTH: 146
<212> TYPE: DNA
<213> ORGANISM: Zea mays

<400> SEQUENCE: 48
actacgaccg tgctcacccg tgccgacgcg ccgtgcatgg tccccgtccc ggctggaacg    60
cgtcctcgga actcggagag agatagagca cagcagacag ggagacaggg atggaaggat    120
ggcgttcgcc cggtacaggt tgctag                                         146

<210> SEQ ID NO 49
<211> LENGTH: 143
<212> TYPE: DNA
<213> ORGANISM: Zea mays

<400> SEQUENCE: 49
ttgcctagca catgcctgcc attgaccgac tgctcagtga gaagtggttc agttgtgctg    60
ttgacagtat agatagatat atatagtagc cctgtagatt ttttttttcag acaaaaaaag    120 aagaagaacg agatgaagtc tgc                                            143

<210> SEQ ID NO 50
<211> LENGTH: 143
<212> TYPE: DNA
<213> ORGANISM: Zea mays

<400> SEQUENCE: 50
ctagcacatg cctgccattg accgactgct cagtgagaag tggttcagtt gtgctgttga    60
cagtatagat agatatatat agtagccctg tagattttttt tttcagacaa aaaagaaga    120 agaacgagat gaagtctgca att                                            143

<210> SEQ ID NO 51
<211> LENGTH: 143
<212> TYPE: DNA
```

<213> ORGANISM: Zea mays

<400> SEQUENCE: 51

| acatgcctgc cattgaccga ctgctcagtg agaagtggtt cagttgtgct gttgacagta | 60 |
| tagatagata tatatagtag ccctgtagat ttttttttca gacaaaaaaa gaagaagaac | 120 |
| gagatgaagt ctgcaattcg gtt | 143 |

<210> SEQ ID NO 52
<211> LENGTH: 146
<212> TYPE: DNA
<213> ORGANISM: Zea mays

<400> SEQUENCE: 52

| catgcctgcc attgaccgac tgctcagtga gaagtggttc agttgtgctg ttgacagtat | 60 |
| agatagatat atatagtagc cctgtagatt tttttttcag acaaaaaaag aagaagaacg | 120 |
| agatgaagtc tgcaattcgg ttttgg | 146 |

<210> SEQ ID NO 53
<211> LENGTH: 143
<212> TYPE: DNA
<213> ORGANISM: Zea mays

<400> SEQUENCE: 53

| gctgttgaca gtatagatag atatatatag tagccctgta gattttttttt tcagacaaaa | 60 |
| aaagaagaag aacgagatga agtctgcaat tcggttttgg cagggcaaat cctgctggac | 120 |
| gggcacgacc tcaggtcgct gga | 143 |

<210> SEQ ID NO 54
<211> LENGTH: 141
<212> TYPE: DNA
<213> ORGANISM: Zea mays

<400> SEQUENCE: 54

| tgacagtata gatagatata tatagtagcc ctgtagattt ttttttcaga caaaaaaga | 60 |
| agaagaacga gatgaagtct gcaattcggt tttggcaggg caaatcctgc tggacgggca | 120 |
| cgacctcagg tcgctggagc t | 141 |

<210> SEQ ID NO 55
<211> LENGTH: 143
<212> TYPE: DNA
<213> ORGANISM: Zea mays

<400> SEQUENCE: 55

| tttttttttc agacaaaaaa agaagaagaa cgagatgaag tctgcaattc ggttttggca | 60 |
| gggcaaatcc tgctggacgg gcacgacctc aggtcgctgg agctgcggtg gctgcggcgg | 120 |
| cagatcgggc tggtgagcca gga | 143 |

<210> SEQ ID NO 56
<211> LENGTH: 138
<212> TYPE: DNA
<213> ORGANISM: Zea mays

<400> SEQUENCE: 56

| aggcggccag ggtggccaac gcccactcct tcatcatcaa actccccgac ggctacgaca | 60 |
| cgcaggtccg tcccgtatag ctagctcact agctgcactg ccacttctct cgcttgctcc | 120 |
| cccaccgttg ctgcctgt | 138 |

<210> SEQ ID NO 57
<211> LENGTH: 134
<212> TYPE: DNA
<213> ORGANISM: Zea mays

<400> SEQUENCE: 57
caacgcccac tccttcatca tcaaactccc cgacggctac gacacgcagg tccgtcccgt        60
atagctagct cactagctgc actgccactt ctctcgcttg ctcccccacc gttgctgcct       120
gttgctctcc aatc                                                         134

<210> SEQ ID NO 58
<211> LENGTH: 134
<212> TYPE: DNA
<213> ORGANISM: Zea mays

<400> SEQUENCE: 58
gcccactcct tcatcatcaa actccccgac ggctacgaca cgcaggtccg tcccgtatag        60
ctagctcact agctgcactg ccacttctct cgcttgctcc cccaccgttg ctgcctgttg       120
ctctccaatc cact                                                         134

<210> SEQ ID NO 59
<211> LENGTH: 133
<212> TYPE: DNA
<213> ORGANISM: Zea mays

<400> SEQUENCE: 59
ctccttcatc atcaaactcc ccgacggcta cgacacgcag gtccgtcccg tatagctagc        60
tcactagctg cactgccact tctctcgctt gctcccccac cgttgctgcc tgttgctctc       120
caatccactt gtc                                                          133

<210> SEQ ID NO 60
<211> LENGTH: 141
<212> TYPE: DNA
<213> ORGANISM: Zea mays

<400> SEQUENCE: 60
cacacgcaca cacacagatc gcctgacaag ccagccattg cttcagatca agaaactgc         60 gtaataattc ctttctttct ttctttcttt cttccagag cacaagggag gggggttata        120
atggctagta cctgactgac t                                                 141

<210> SEQ ID NO 61
<211> LENGTH: 143
<212> TYPE: DNA
<213> ORGANISM: Zea mays

<400> SEQUENCE: 61
agccagccat tgcttcagat caaagaaact gcgtaataat tcctttcttt ctttctttct        60
ttctttccag agcacaaggg aggggggtta atggctag tacctgactg actgtacgag        120
ccgagattaa cggcagtcac ctc                                               143

<210> SEQ ID NO 62
<211> LENGTH: 143
<212> TYPE: DNA
<213> ORGANISM: Zea mays

<400> SEQUENCE: 62

```
atcgccctgc tggccatttg gcaccaccta gtcgtacatg tgttcagtca tttccgtcca    60
ttactactac gaccgtgctc acccgtgccg acgcgccgtg catggtcccc gtcccggctg   120
gaacgcgtcc tcggaagaga gag                                           143

<210> SEQ ID NO 63
<211> LENGTH: 143
<212> TYPE: DNA
<213> ORGANISM: Zea mays

<400> SEQUENCE: 63
ccattactac tacgaccgtg ctcacccgtg ccgacgcgcc gtgcatggtc cccgtcccgg    60
ctggaacgcg tcctcggaag agagagatag agcacagcag acagggagac agggatggaa   120
ggatggcgtt cgcccggtac agg                                           143

<210> SEQ ID NO 64
<211> LENGTH: 143
<212> TYPE: DNA
<213> ORGANISM: Zea mays

<400> SEQUENCE: 64
cattactact acgaccgtgc tcacccgtgc cgacgcgccg tgcatggtcc ccgtcccggc    60
tggaacgcgt cctcggaaga gagagataga gcacagcaga cagggagaca gggatggaag   120
gatggcgttc gcccggtaca ggt                                           143

<210> SEQ ID NO 65
<211> LENGTH: 143
<212> TYPE: DNA
<213> ORGANISM: Zea mays

<400> SEQUENCE: 65
attactacta cgaccgtgct cacccgtgcc gacgcgccgt gcatggtccc cgtcccggct    60
ggaacgcgtc ctcggaagag agagatagag cacagcagac agggagacag ggatggaagg   120
atggcgttcg cccggtacag gtt                                           143

<210> SEQ ID NO 66
<211> LENGTH: 143
<212> TYPE: DNA
<213> ORGANISM: Zea mays

<400> SEQUENCE: 66
ttactactac gaccgtgctc acccgtgccg acgcgccgtg catggtcccc gtcccggctg    60
gaacgcgtcc tcggaagaga gagatagagc acagcagaca gggagacagg gatggaagga   120
tggcgttcgc ccggtacagg ttg                                           143

<210> SEQ ID NO 67
<211> LENGTH: 143
<212> TYPE: DNA
<213> ORGANISM: Zea mays

<400> SEQUENCE: 67
tactactacg accgtgctca cccgtgccga cgcgccgtgc atggtcccg tcccggctgg     60 aacgcgtcct cggaagagag agatagagca cagcagacag ggagacaggg atggaaggat   120
ggcgttcgcc cggtacaggt tgc                                           143

<210> SEQ ID NO 68
<211> LENGTH: 143
```

```
<212> TYPE: DNA
<213> ORGANISM: Zea mays

<400> SEQUENCE: 68
ctactacgac cgtgctcacc cgtgccgacg cgccgtgcat ggtccccgtc ccggctggaa    60
cgcgtcctcg gaagagagag atagagcaca gcagacaggg agacagggat ggaaggatgg   120
cgttcgcccg gtacaggttg cta                                          143

<210> SEQ ID NO 69
<211> LENGTH: 143
<212> TYPE: DNA
<213> ORGANISM: Zea mays

<400> SEQUENCE: 69
tactacgacc gtgctcaccc gtgccgacgc gccgtgcatg gtccccgtcc cggctggaac    60
gcgtcctcgg aagagagaga tagagcacag cagacaggga gacagggatg gaaggatggc   120
gttcgcccgg tacaggttgc tag                                          143

<210> SEQ ID NO 70
<211> LENGTH: 142
<212> TYPE: DNA
<213> ORGANISM: Zea mays

<400> SEQUENCE: 70
actacgaccg tgctcacccg tgccgacgcg ccgtgcatgg tccccgtccc ggctggaacg    60
cgtcctcgga agagagagat agagcacagc agacagggag acaggatgg aaggatggcg   120 ttcgcccggt acaggttgct ag                                           142

<210> SEQ ID NO 71
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 71
caggaggcgc tggaccgctt catgatcggg cgcaccaccc tggtgatcgc gcacaggctg    60
tccaccatcc gnaaggccga cgtggtggcc gtgctgcagg cggcgccgt ctccgagatg   120 ggcgcgcacg acgagctgat ggc                                          143

<210> SEQ ID NO 72
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 72
tccatcggct ccatggtctg cggctccttc agcgccatct tcgcctacat cctcagcgcc    60
gtgctcagcg tntactacgc gccggacccg cggtacatga agcgcgagat cgcaaaatac   120
tgctacctgc tcatcggcat gtc                                          143

<210> SEQ ID NO 73
<211> LENGTH: 143
<212> TYPE: DNA
```

<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 73
gcctacatcc tcagcgccgt gctcagcgtc tactacgcgc cggacccgcg gtacatgaag    60
cgcgagatcg cnaaatactg ctacctgctc atcggcatgt cctccgcggc gctgctgttc   120
aacacggtgc agcacgtgtt ctg                                           143

<210> SEQ ID NO 74
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 74
ctggttcgac gcggacgaga acgccagcgc gcgcgtggcc gccaggctag cgctggacgc    60
ccagaacgtg cnctccgcca tcggggaccg catctccgtc atcgtccaga actcggcgct   120
gatgctggtg gcctgcaccg cgg                                           143

<210> SEQ ID NO 75
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g, t, deletion, or insertion

<400> SEQUENCE: 75
cagaacgtgc gctccgccat cggggaccgc atctccgtca tcgtccagaa ctcggcgctg    60
atgctggtgg cntgcaccgc ggggttcgtc ctccagtggc gcctcgcgct cgtgctcctc   120
gccgtgttcc cgctcgtcgt ggg                                           143

<210> SEQ ID NO 76
<211> LENGTH: 143
<212> TYPE: DNA
<213> ORGANISM: Zea mays

<400> SEQUENCE: 76
caggaggcgc tggaccgctt catgatcggg cgcaccaccc tggtgatcgc gcacaggctg    60
tccaccatcc gaaaggccga cgtggtggcc gtgctgcagg gcggcgccgt ctccgagatg   120
ggcgcgcacg acgagctgat ggc                                           143

<210> SEQ ID NO 77
<211> LENGTH: 143
<212> TYPE: DNA
<213> ORGANISM: Zea mays

<400> SEQUENCE: 77
tccatcggct ccatggtctg cggctccttc agcgccatct tcgcctacat cctcagcgcc    60
gtgctcagcg tgtactacgc gccggacccg cggtacatga agcgcgagat cgcaaaatac   120
tgctacctgc tcatcggcat gtc                                           143

<210> SEQ ID NO 78
<211> LENGTH: 143
<212> TYPE: DNA
<213> ORGANISM: Zea mays

<400> SEQUENCE: 78
gcctacatcc tcagcgccgt gctcagcgtc tactacgcgc cggacccgcg gtacatgaag    60
cgcgagatcg ccaaatactg ctacctgctc atcggcatgt cctccgcggc gctgctgttc   120
aacacggtgc agcacgtgtt ctg                                           143

<210> SEQ ID NO 79
<211> LENGTH: 143
<212> TYPE: DNA
<213> ORGANISM: Zea mays

<400> SEQUENCE: 79
ctggttcgac gcggacgaga acgccagcgc gcgcgtggcc gccaggctag cgctggacgc    60
ccagaacgtg ctctccgcca tcggggaccg catctccgtc atcgtccaga actcggcgct   120
gatgctggtg gcctgcaccg cgg                                           143

<210> SEQ ID NO 80
<211> LENGTH: 143
<212> TYPE: DNA
<213> ORGANISM: Zea mays

<400> SEQUENCE: 80
cagaacgtgc gctccgccat cggggaccgc atctccgtca tcgtccagaa ctcggcgctg    60
atgctggtgg cgtgcaccgc ggggttcgtc ctccagtggc gcctcgcgct cgtgctcctc   120
gccgtgttcc cgctcgtcgt ggg                                           143

<210> SEQ ID NO 81
<211> LENGTH: 143
<212> TYPE: DNA
<213> ORGANISM: Zea mays

<400> SEQUENCE: 81
caggaggcgc tggaccgctt catgatcggg cgcaccaccc tggtgatcgc gcacaggctg    60
tccaccatcc gcaaggccga cgtggtggcc gtgctgcagg gcggcgccgt ctccgagatg   120
ggcgcgcacg acgagctgat ggc                                           143

<210> SEQ ID NO 82
<211> LENGTH: 143
<212> TYPE: DNA
<213> ORGANISM: Zea mays

<400> SEQUENCE: 82
tccatcggct ccatggtctg cggctccttc agcgccatct tcgcctacat cctcagcgcc    60
gtgctcagcg tctactacgc gccgacccgc ggtacatga agcgcgagat cgcaaaatac   120
tgctacctgc tcatcggcat gtc                                           143

<210> SEQ ID NO 83
<211> LENGTH: 143
<212> TYPE: DNA
<213> ORGANISM: Zea mays

<400> SEQUENCE: 83
gcctacatcc tcagcgccgt gctcagcgtc tactacgcgc cggacccgcg gtacatgaag    60

```
cgcgagatcg caaaatactg ctacctgctc atcggcatgt cctccgcggc gctgctgttc    120
aacacggtgc agcacgtgtt ctg                                            143
```

<210> SEQ ID NO 84
<211> LENGTH: 143
<212> TYPE: DNA
<213> ORGANISM: Zea mays

<400> SEQUENCE: 84

```
ctggttcgac gcggacgaga acgccagcgc gcgcgtggcc gccaggctag cgctggacgc     60
ccagaacgtg cgctccgcca tcggggaccg catctccgtc atcgtccaga actcggcgct    120
gatgctggtg gcctgcaccg cgg                                            143
```

<210> SEQ ID NO 85
<211> LENGTH: 143
<212> TYPE: DNA
<213> ORGANISM: Zea mays

<400> SEQUENCE: 85

```
cagaacgtgc gctccgccat cggggaccgc atctccgtca tcgtccagaa ctcggcgctg     60
atgctggtgg cctgcaccgc ggggttcgtc ctccagtggc gcctcgcgct cgtgctcctc    120
gccgtgttcc cgctcgtcgt ggg                                            143
```

<210> SEQ ID NO 86
<211> LENGTH: 143
<212> TYPE: DNA
<213> ORGANISM: Zea mays
<220> FEATURE:
<221> NAME/KEY: misc_feature
<222> LOCATION: (72)..(77)
<223> OTHER INFORMATION: n is a, c, g, t, deletion, or insertion

<400> SEQUENCE: 86

```
ttgcctagca catgcctgcc attgaccgac tgctcagtga gaagtggttc agttgtgctg     60
ttgacagtat annnnnntat atatagtagc cctgtagatt tttttttcag acaaaaaaag    120
aagaagaacg agatgaagtc tgc                                            143
```

<210> SEQ ID NO 87
<211> LENGTH: 148
<212> TYPE: DNA
<213> ORGANISM: Zea mays
<220> FEATURE:
<221> NAME/KEY: misc_feature
<222> LOCATION: (76)..(77)
<223> OTHER INFORMATION: n is a, c, g, t, deletion, or insertion

<400> SEQUENCE: 87

```
catgcctgcc attgaccgac tgctcagtga gaagtggttc agttgtgctg ttgacagtat     60
agatagatat atatanngta gccctgtaga tttttttttc agacaaaaaa agaagaagaa    120
cgagatgaag tctgcaattc ggttttgg                                       148
```

<210> SEQ ID NO 88
<211> LENGTH: 142
<212> TYPE: DNA
<213> ORGANISM: Zea mays
<220> FEATURE:
<221> NAME/KEY: misc_feature
<222> LOCATION: (66)..(69)
<223> OTHER INFORMATION: n is a, c, g, t, deletion, or insertion

<400> SEQUENCE: 88

```
caacgcccac tccttcatca tcaaactccc cgacggctac gacacgcagg tccgtcccgt    60
atagcnnnnt agctcactag ctgcactgcc acttctctcg cttgctcccc caccgttgct   120
gcctgttgct ctccaatcca ct                                            142
```

<210> SEQ ID NO 89
<211> LENGTH: 146
<212> TYPE: DNA
<213> ORGANISM: Zea mays
<220> FEATURE:
<221> NAME/KEY: misc_feature
<222> LOCATION: (71)..(76)
<223> OTHER INFORMATION: n is a, c, g, t, deletion, or insertion

<400> SEQUENCE: 89

```
tttctagagt ttaaagctta tcttagaata aatgcatctt tagctacgag acaacctaac    60
ttcagttgtt nnnnnngttt tttttacttt ctctcttctc acaaatacta tgattacgtc   120
tttacagcga tctttttat tccaaa                                         146
```

<210> SEQ ID NO 90
<211> LENGTH: 146
<212> TYPE: DNA
<213> ORGANISM: Zea mays
<220> FEATURE:
<221> NAME/KEY: misc_feature
<222> LOCATION: (77)..(77)
<223> OTHER INFORMATION: n is a, c, g, t, deletion, or insertion

<400> SEQUENCE: 90

```
tttctagagt ttaaagctta tcttagaata aatgcatctt tagctacgag acaacctaac    60
ttcagttgtt gttgttnttt tttttacttt ctctcttctc acaaatacta tgattacgtc   120
tttacagcga tctttttat tccaaa                                         146
```

<210> SEQ ID NO 91
<211> LENGTH: 105
<212> TYPE: DNA
<213> ORGANISM: Zea mays
<220> FEATURE:
<221> NAME/KEY: misc_feature
<222> LOCATION: (60)..(61)
<223> OTHER INFORMATION: n is a, c, g, t, deletion, or insertion

<400> SEQUENCE: 91

```
attccaaacc taaaaatgca tgcactcact ctaaaagcgc aaagggagca tctttttttn    60 nccccccatca tctgcacgca gccttttctt ttcctcatgt cacga                  105
```

<210> SEQ ID NO 92
<211> LENGTH: 181
<212> TYPE: DNA
<213> ORGANISM: Zea mays
<220> FEATURE:
<221> NAME/KEY: misc_feature
<222> LOCATION: (63)..(111)
<223> OTHER INFORMATION: n is a, c, g, t, deletion, or insertion

<400> SEQUENCE: 92

```
tcggtgctgg ctctggtgca gcggttctac gagcccacgt ccgggcgcgt gctcctggac    60
ggnnnnnnnn nnnnnnnnnn nnnnnnnnnn nnnnnnnnnn nnnnnnnnnn ncaaggacgt   120
gcgcaagtac aacctgcggg cgctgcggcg cgtggtggcg gtggtaccgc aggagccgtt   180
c                                                                   181
```

<210> SEQ ID NO 93
<211> LENGTH: 185
<212> TYPE: DNA
<213> ORGANISM: Zea mays
<220> FEATURE:
<221> NAME/KEY: misc_feature
<222> LOCATION: (51)..(135)
<223> OTHER INFORMATION: n is a, c, g, t, deletion, or insertion

<400> SEQUENCE: 93

```
agaacacgga ctcacactcc cataactata actgacttga tcatgattcc nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnatttt attaacaatt caatttttat ttattaatta cgtctggacg   180
aggag                                                               185
```

<210> SEQ ID NO 94
<211> LENGTH: 140
<212> TYPE: DNA
<213> ORGANISM: Zea mays
<220> FEATURE:
<221> NAME/KEY: misc_feature
<222> LOCATION: (52)..(69)
<223> OTHER INFORMATION: n is a, c, g, t, deletion, or insertion

<400> SEQUENCE: 94

```
ccaccgtcag ggaataagac ttattatttt attaacaatt caatttttat tnnnnnnnnn    60
nnnnnnnnnt attaattacg tctggacgag gagtactggt ttatttgatg agagacatgg   120
cagtccaagt caaactcgtt                                               140
```

<210> SEQ ID NO 95
<211> LENGTH: 711
<212> TYPE: DNA
<213> ORGANISM: Zea mays
<220> FEATURE:
<221> NAME/KEY: misc_feature
<222> LOCATION: (66)..(644)
<223> OTHER INFORMATION: n is a, c, g, t, deletion, or insertion

<400> SEQUENCE: 95

```
actgaaggtg tgtatgcagc gtcaagtcat ccatccgttc cactccactc actcatgcgt    60
cgcgcnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnnnnnnn nnnnnnnnnn   240
nnnnnnnnnn nnnnnnnnnn nnnnnnnnnn nnnnnnnnnn nnnnnnnnnn nnnnnnnnnn   300
nnnnnnnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnactctg cgctcgtgcc   660
tgcccggggc taaagcttta gtagctagcc tcagatcaga tactgttcgt g            711
```

<210> SEQ ID NO 96
<211> LENGTH: 114
<212> TYPE: DNA
<213> ORGANISM: Zea mays

-continued

```
<220> FEATURE:
<221> NAME/KEY: misc_feature
<222> LOCATION: (68)..(80)
<223> OTHER INFORMATION: n is a, c, g, t, delection, or insertion

<400> SEQUENCE: 96
gcactcagga ctcgcagcga gagaattttt ttaatcaagc ctaaaattca ctttcggaca      60
aatcgaannn nnnnnnnnnn ctactcataa atattaacca tgagaccttt tcgc           114

<210> SEQ ID NO 97
<211> LENGTH: 141
<212> TYPE: DNA
<213> ORGANISM: Zea mays
<220> FEATURE:
<221> NAME/KEY: misc_feature
<222> LOCATION: (71)..(71)
<223> OTHER INFORMATION: n is a, c, g, t, delection, or insertion

<400> SEQUENCE: 97
ttagcgcatt aatctgagga tgtccagttc gcttgcttgc caatcgccat tgccatcgca      60
acaacaatac ntcgccaact gccattgctg ggtagactag tacagtagca gttagaagaa    120
gcctccactg tacattgcat t                                              141

<210> SEQ ID NO 98
<211> LENGTH: 141
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, t, delection, or insertion

<400> SEQUENCE: 98
ttagcgcatt aatctgagga tgtccagttc gcttgcttgc caatcgccat tgccatcgca      60
acaacaatac ttngccaact gccattgctg ggtagactag tacagtagca gttagaagaa    120
gcctccactg tacattgcat t                                              141

<210> SEQ ID NO 99
<211> LENGTH: 144
<212> TYPE: DNA
<213> ORGANISM: Zea mays
<220> FEATURE:
<221> NAME/KEY: misc_feature
<222> LOCATION: (72)..(73)
<223> OTHER INFORMATION: n is a, c, g, t, delection, or insertion

<400> SEQUENCE: 99
ccatcctctt tcttgctttt cttttactt tctttggtcg tggctgtttg tggtcataca      60
tacattcacg cnnagagcag aagagctagc taagctaggt gggtgtgcct gcaacgcggg    120
acaaagaaaa ctatttgttg cctg                                           144

<210> SEQ ID NO 100
<211> LENGTH: 138
<212> TYPE: DNA
<213> ORGANISM: Zea mays
<220> FEATURE:
<221> NAME/KEY: misc_feature
<222> LOCATION: (70)..(70)
<223> OTHER INFORMATION: n is a, c, g, t, delection, or insertion

<400> SEQUENCE: 100
tgtgtctgtc cacccagct cttgctactc tacttactac tgtgctacta gtggtagggt      60
```

```
aggtatcttn cataaactgt tattataaac tgtcatctga gaaagagagc cagtcaaacc    120
catgctgctg cttatttt                                                 138

<210> SEQ ID NO 101
<211> LENGTH: 142
<212> TYPE: DNA
<213> ORGANISM: Zea mays
<220> FEATURE:
<221> NAME/KEY: misc_feature
<222> LOCATION: (70)..(70)
<223> OTHER INFORMATION: n is a, c, g,  t, deletion, or insertion

<400> SEQUENCE: 101
tcttacataa actgttatta taaactgtca tctgagaaag agagccagtc aaacccatgc    60
tgctgcttan ttttaatcac tgtcaaatgg caggcaggca ggcagtctgg ttagttaata   120
acatctggga agggtttaat ca                                           142

<210> SEQ ID NO 102
<211> LENGTH: 141
<212> TYPE: DNA
<213> ORGANISM: Zea mays
<220> FEATURE:
<221> NAME/KEY: misc_feature
<222> LOCATION: (70)..(70)
<223> OTHER INFORMATION: n is a, c, g,  t, deletion, or insertion

<400> SEQUENCE: 102
ggcaggcagg caggcagtct ggttagttaa taacatctgg gaagggttta atcaaaccaa    60
atcaaatcan acgaaatcta gaggccacat gggatggggc catatgtact gtactagcat   120
aactagcggc tagattttat t                                            141

<210> SEQ ID NO 103
<211> LENGTH: 141
<212> TYPE: DNA
<213> ORGANISM: Zea mays
<220> FEATURE:
<221> NAME/KEY: misc_feature
<222> LOCATION: (71)..(71)
<223> OTHER INFORMATION: n is a, c, g,  t, deletion, or insertion

<400> SEQUENCE: 103
caaaccaaat caaatcagac gaaatctaga ggccacatgg gatggggcca tatgtactgt    60
actagcataa ntagcggcta gattttatta gaacacggac tcacactccc ataactataa   120
ctgacttgat catgattcct t                                            141

<210> SEQ ID NO 104
<211> LENGTH: 143
<212> TYPE: DNA
<213> ORGANISM: Zea mays
<220> FEATURE:
<221> NAME/KEY: misc_feature
<222> LOCATION: (72)..(72)
<223> OTHER INFORMATION: n is a, c, g,  t, deletion, or insertion

<400> SEQUENCE: 104
tactgtacta gcataactag cggctagatt ttattagaac acggactcac actcccataa    60
ctataactga cnttgatcat gattccttgc caagcaatgc tcgcatgccc atgcatgcat   120
catccctggt caaactcaaa cac                                          143

<210> SEQ ID NO 105
<211> LENGTH: 141
```

```
<212> TYPE: DNA
<213> ORGANISM: Zea mays
<220> FEATURE:
<221> NAME/KEY: misc_feature
<222> LOCATION: (71)..(71)
<223> OTHER INFORMATION: n is a, c, g, t, delection, or insertion

<400> SEQUENCE: 105
catcatccct ggtcaaactc aaacactctc caccgtcagg gaataagact tattatttta    60
ttaacaattc nattttatt tattaattac gtctggacga ggagtactgg tttatttgat   120
gagagacatg gcagtccaag t                                             141

<210> SEQ ID NO 106
<211> LENGTH: 141
<212> TYPE: DNA
<213> ORGANISM: Zea mays
<220> FEATURE:
<221> NAME/KEY: misc_feature
<222> LOCATION: (71)..(71)
<223> OTHER INFORMATION: n is a, c, g, t, delection, or insertion

<400> SEQUENCE: 106
aacactctcc accgtcaggg aataagactt attatttat taacaattca atttttattt    60
attaattacg nctggacgag gagtactggt ttatttgatg agagacatgg cagtccaagt   120
caaactcgtt tgtctgacca t                                             141

<210> SEQ ID NO 107
<211> LENGTH: 139
<212> TYPE: DNA
<213> ORGANISM: Zea mays
<220> FEATURE:
<221> NAME/KEY: misc_feature
<222> LOCATION: (71)..(71)
<223> OTHER INFORMATION: n is a, c, g, t, delection, or insertion

<400> SEQUENCE: 107
gggaataaga cttattattt tattaacaat tcaattttta tttattaatt acgtctggac    60
gaggagtact ngtttatttg atgagagaca tggcagtcca agtcaaactc gtttgtctga   120
ccatggcggt gatggccgg                                                139

<210> SEQ ID NO 108
<211> LENGTH: 134
<212> TYPE: DNA
<213> ORGANISM: Zea mays
<220> FEATURE:
<221> NAME/KEY: misc_feature
<222> LOCATION: (68)..(68)
<223> OTHER INFORMATION: n is a, c, g, t, delection, or insertion

<400> SEQUENCE: 108
tttatttgat gagagacatg gcagtccaag tcaaactcgt tgtctgacc atggcggtga    60 tggccggntg caggttgggg agcgcggcct gcagctctcc ggtgggcaga agcagcgcat   120
cgccatcgcc cgcg                                                     134

<210> SEQ ID NO 109
<211> LENGTH: 141
<212> TYPE: DNA
<213> ORGANISM: Zea mays
<220> FEATURE:
<221> NAME/KEY: misc_feature
<222> LOCATION: (65)..(74)
<223> OTHER INFORMATION: n is a, c, g, t, delection, or insertion
```

<400> SEQUENCE: 109

```
gtcgtacatg tgttcagtca tttccgtcca ttactactac gaccgtgctc acccgtgccg    60
acgcnnnnnn nnnngccgtg catggtcccc gtcccggctg gaacgcgtcc tcggaagaga   120
gagatagagc acagcagaca g                                             141
```

<210> SEQ ID NO 110
<211> LENGTH: 579
<212> TYPE: DNA
<213> ORGANISM: Zea mays

<400> SEQUENCE: 110

```
caggcccgta tatggcccag tgcaactggg ccgacggaac caggccacca atatcagtag    60
gcctccaatt atgaattctc catatacacg tggtccatgt atgctgatcc aggatatact   120
tggcctccaa atttgtgcat tacgattgga attctaggct ttgtttcttc cttccgtagt   180
tccgccaatc tcgctagctg aaacgacgcc gatctgggag tgcgccgcca ccacaaacgc   240
tccatcgcca gtcatcacgc catcgatgcc gagctactat ggggccgtga tctcgccgtt   300
gccgacgctt tgacctttgc cgcacctaga cgttgcaagg tcgacgcaac aagccaatcg   360
agactgcagg tatgtgatca ggaaacactc cattgttttt ttcctttgct tgcaaattgc   420
aatcgatagg caaatgattt acttataaaa ctaaagttta tgttagttaa ttctccaatc   480
taaatacata tggttaattg caatattata taaatatagg cctccacttt gtgttttgca   540
ccaggccaaa ataaactcag gtacgggcct gcgtcgcgc                          579
```

<210> SEQ ID NO 111
<211> LENGTH: 4187
<212> TYPE: DNA
<213> ORGANISM: Zea mays
<220> FEATURE:
<221> NAME/KEY: misc_feature
<222> LOCATION: (2308)..(2310)
<223> OTHER INFORMATION: n is a, c, g, t, deletion, or insertion
<220> FEATURE:
<221> NAME/KEY: misc_feature
<222> LOCATION: (2308)..(2310)
<223> OTHER INFORMATION: Additional sequence insertion of undetermined
      size

<400> SEQUENCE: 111

```
tgaaagcgga ctacggttac taccgttccg ctgtgaccgg gtctcttgcg tatactccca    60
cgactcgcac tactccgtat tgtacgcacc actccaacgg catagtgtgc gcaccactca   120
aggacccagt cctctcggtg cccagttcat gtaatctata tatgcactat gagttatcaa   180
tacagatagt tagttcatcg tattcattct acatggtatc agccttcttc gttcctacag   240
caatcctgtg tctcaccttc cacatcaatg gctcactccc cactccctc cgatgactcc    300
tctgatgacg agctcgtcgt tccagcaccc gcttccgtta tccaaagcat tcccatccgc   360
cagcacgttc ctgtcgtcct cgacatggat gaggggaact atgggcaatg gcgatgcttc   420
tttgaatctg cgctcggaaa attcggcctc accagccatg ttcgttcttc cacccccatac  480
cgtgaccgtc ctggtgactg gcgcatggtg gattcctgta ttgccaactg gatcctcacc   540
acagtctcca agggcgtctt cgacatcatc cgtcgcgacc gcaatgacgc cttctctctg   600
tggcacgcca tcgaagacct gtttcaagac aacgaacttc agcgtgctgt gtaccttgaa   660
gccgagctgc gttccctgca gcaaggcgac ttgtcgatga atgcctactg caccaagttg   720
aagcgtctcg ccgatcaact tcgcgacatc ggccatcccg tctccgaacc cagtcaggtg   780
```

```
ctcaaccttc ttcgcgggct caatccaaag taccgctacg tcaagccgt  gatcacctcc    840 aagttcccag cgcacacctt catgagcgct cgatccttcc tcatgcttga ggaggccagc    900
atcgaacacg atgtcgccgt tgaggccacc cacgcactga ctgtcacaca tggtgactcg    960
tccagtgctg ttcctccatc tgcatcttct ggcaccagga caactcctc  ctcctccaac   1020 acgccacgcc gtgacaatcg cttcaacgct ggtagcacct cccattctac caatcgatct   1080
gatcgcaggc gcggtcgcgg caacggcggt cgtggacgct caacaacca  gtctggacca   1140 tggacagcag gtctcaatcc atggcaaggc atggttcagg catggcaaat gccttccgt    1200 gcacccggag caggcgttct ggggccacgc ccgccgttcc aacctcagca agccatggca   1260
gcctatcatc agccacctcc tgcatctgcc ggcaccttcg acaacagcgc tctttatgcg   1320
gcactgcagg ctgccgcagt tccaactcat ccgcccaaca cttctgactg gtacttcgac   1380
accggtgcgt cgtcgcacat gtcgtcttcc cctggtaact ttccaccctc ttcccttctc   1440
cccttttcgt cttccataac agtgggtaat ggtgcccagc tacctgttac acatcatgca   1500
cacacatcca ttcctactgc cacttctcct cttcagttac atgatgttct tatttccccg   1560
tcactcgtta aaaatttggt ttctgttcgc cgtcttactc gtgataataa tgtttccatt   1620
gaatttgacc cttgtggttt ttctatcaag gatcttcctt ccaaagcgga gattctccga   1680
tgtgagagca atggcgatct ctatccactc cgtcttcccc accagcatgc tctcactgct   1740
tcctcgatgg cgtcgctatg gcatcagcga ctgggtcatc ctggacaacc agtcacctcc   1800
catattttaa aatccctgtc ttttcaatgt aataaagctg atgctcattc ctgctcctct   1860
tgtcgattgg gcaaacatac tagattacct tttcgtgttt ctgaatcacg ttcattttt    1920 ccttttcaac tagttcattc agacgtctgg acatctcctt gttatagtta ttccggatat   1980
aaatattatg ttatttttct ggatgattat acacattatc tttggagcat cccctccgc    2040 aacaaatctg acgttttcc  tactgttaga gcgttcatat cttatgttca tactcaattc   2100
cacctcccta ttcttgcgtt tcagactgat aacggtgggg aatatgattc tactgctatg   2160
cgccttcttc tgtcatctct tggcacccaa ctacgtcttt cttgtccata cacatcccag   2220
caaaatggga aagctgagag aatacttcgc actgtcaatg attgcctgcg tacactacta   2280
atccatagtg cagctcctct cgcacttnnn acgccatcat cgcccaccaa tcacccgact   2340
catccaatgg tgactcgtgc acgcgcaggg atctccaagc ctaacccgaa gtacgccttc   2400
gtgaccacgg agacaatatc gccgattcct cgcagcgttc gcaccgctgt caaagatccc   2460
cattggtatg ctgcaatgaa gtccgaattt gatgcactgc aagccaacca cacttggact   2520
cttgtctctc ggcctccagg tgctcggatc atcaccggca aatgggtctt caagcacaag   2580
atgaatccag acggcaccct cgcgcgatac aaggcacgtt gggtcgtccg tgggttcaac   2640
cagcggcccg gtgttgattt cggggagacg ttctcgccgg tgatcaagcc ggccacgatt   2700
cgtaccgtgc tgacgcttgt ggctactcac aactggccag ctcaccaact tgacgtctcc   2760
aacgctttcc tccacggcaa ccttcaagaa caggtgtaca gtcagcaacc cactgggttt   2820
gttgatccca gccgcccaga tgacgtctgc ctgctctcca ggtcgctcta tggtctccgt   2880
caggcaccac gggcatggtt ccagcgtttc gtcgagcacg tgacatccct cggcttcatt   2940
caatcgaagg ccgattcatc gctcttcgtg tatcaccacc atggcgagac agcttatctt   3000
cttctctacg tcgacgacat gatcctttct gcctcgacac gtcgtctggt ccagcatgtc   3060
atcgcgcgtc tacacgatgc cttcgctgtg aaggatatgg ggcctgttca ccattttctc   3120
ggcatcggcg ttcgacggaa ccgcaccggc ttcttcctct ctcaaggaca gtatgctgaa   3180
```

```
gatctcctcg agcgtgcagg aatgacgaac tgcaaacctg ttgccacccc tgccgacacc    3240
caacagaagg catccgctgg cgatggcata ctgctcgacg acgccacttc ataccgtagt    3300
atcgtcggcg ccctgcagta cttgacgatc acccgtccgg acattgccta cgccgtgcag    3360
caggtgtgtc tccacatgca cgcgccgcgg gacgtgcatc tcaccatgct caagcgtatt    3420
ctccggtaca tcaagggcac catccacttc ggcatccagc tgcgcactgc ctcgccttcg    3480
acgatcactg catactccga cgccgactgg gcaggctgcc ccgacacacg cgctctaca    3540 tcgggtttct gcatcttctt cggcaactcc ctcgtctcat ggtcgtctaa acgacagacc    3600
accgtctctc ggtccagcgc agaagctgag tatcgggcca tcgccaacgc catcgccgaa    3660
tgctcctggc ttcgccacct cctttctgag ctgctttaca gggtcccctc agcaacagtg    3720
gcattctgcg acaacatctc ttcggtgtac atggcacgca atcccgttca tcatcggcgc    3780
actaagcata tcgagctgga catccatttt gtgcgggaaa aggtcgccat tggtgagttg    3840
catgttacgc acattcccag tgcgcgacaa atcgagatg tgttcaccaa aggtctacct    3900
tcggcactgt tcaacgactt cagagacagc ctctccgtca ccaacgcgac cgtcgagact    3960 gcagggggt gaaagcggac tacggttact accgttccgc tgtgaccggg tctcttgcgt    4020
atactcccac gactcgcact actccgtatt gtacgcacca ctccaacggc atagtgtgcg    4080
caccactcaa ggacccagtc ctctcggtgc ccagttcatg taatctatat atgcactatg    4140
agttatcaat acagatagtt agttcatcgt attcattcta cagacgg                 4187

<210> SEQ ID NO 112
<211> LENGTH: 21
<212> TYPE: DNA
<213> ORGANISM: Zea mays

<400> SEQUENCE: 112
catccgttcc actccactca c                                              21

<210> SEQ ID NO 113
<211> LENGTH: 28
<212> TYPE: DNA
<213> ORGANISM: Zea mays

<400> SEQUENCE: 113
atctgaggct agctactaaa gctttagc                                       28

<210> SEQ ID NO 114
<211> LENGTH: 23
<212> TYPE: DNA
<213> ORGANISM: Zea mays

<400> SEQUENCE: 114
tggaggccaa gtatatcctg gat                                            23

<210> SEQ ID NO 115
<211> LENGTH: 16
<212> TYPE: DNA
<213> ORGANISM: Zea mays

<400> SEQUENCE: 115
tcatgcgtcg cgcact                                                    16

<210> SEQ ID NO 116
<211> LENGTH: 15
<212> TYPE: DNA
```

```
<213> ORGANISM: Zea mays

<400> SEQUENCE: 116
aggcccgtat atggc                                                    15

<210> SEQ ID NO 117
<211> LENGTH: 18
<212> TYPE: DNA
<213> ORGANISM: Zea mays

<400> SEQUENCE: 117
aacaattcca tttttatt                                                 18

<210> SEQ ID NO 118
<211> LENGTH: 85
<212> TYPE: DNA
<213> ORGANISM: Zea mays

<400> SEQUENCE: 118
ttgccaagca atgctcgcat gcccatgcat gcatcatccc tggtcaaact caaacactct   60
ccaccgtcag ggaataagac ttatt                                         85

<210> SEQ ID NO 119
<211> LENGTH: 13
<212> TYPE: DNA
<213> ORGANISM: Zea mays

<400> SEQUENCE: 119
cctggaacgg gtg                                                      13

<210> SEQ ID NO 120
<211> LENGTH: 10
<212> TYPE: DNA
<213> ORGANISM: Zea mays

<400> SEQUENCE: 120
gccgtgccga                                                          10
```